United States Patent
Wong et al.

(10) Patent No.: US 9,623,080 B2
(45) Date of Patent: Apr. 18, 2017

(54) METHODS FOR TREATING OR PREVENTING FATTY LIVER DISEASE USING CTRP3

(71) Applicant: THE JOHNS HOPKINS UNIVERSITY, Baltimore, MD (US)

(72) Inventors: G. William Wong, Lutherville-Timonium, MD (US); Jonathan M. Peterson, Johnson City, TN (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 14/777,001

(22) PCT Filed: Mar. 12, 2014

(86) PCT No.: PCT/US2014/024193
§ 371 (c)(1),
(2) Date: Sep. 15, 2015

(87) PCT Pub. No.: WO2014/150772
PCT Pub. Date: Sep. 25, 2014

(65) Prior Publication Data
US 2016/0175396 A1     Jun. 23, 2016

Related U.S. Application Data

(60) Provisional application No. 61/789,430, filed on Mar. 15, 2013.

(51) Int. Cl.
*A61P 3/06*     (2006.01)
*C07K 14/47*    (2006.01)
*A61K 38/19*    (2006.01)

(52) U.S. Cl.
CPC ............ *A61K 38/191* (2013.01); *C07K 14/47* (2013.01)

(58) Field of Classification Search
None
See application file for complete search history.

(56) References Cited

U.S. PATENT DOCUMENTS

2004/0248156 A1  12/2004  Hu et al.
2012/0122959 A1   5/2012  Stoffel et al.

OTHER PUBLICATIONS

Schäffler et al., "Mechanisms of Disease: adipocytokines and visceral adipose tissue—emerging role in nonalcoholic fatty liver disease" Nat. Rev. Gastroenterol. Hepat. 2:273-280 (2005).*
Schäffler et al., "CTRP family: linking immunity to metabolism," Trends Endocrin. Metab. 23:194-204 (2012).*
Weigert et al., "The adiponectin paralog CORS-26 has anti-inflammatory properties and is produced by human monocytic cells," FEBS Lett. 579: 5565-5570 (2005).*
Nonalcoholic steatohepatitis (NASH), Merck Manual, accessed Jul. 29, 2016 at URL merckmanual.com, pp. 1-3.*
Pizer, E. S., C. Jackisch, F. D. Wood, G. R. Pasternack, N. E. Davidson, and F. P. Kuhajda. 1996. Inhibition of fatty acid synthesis induces programmed cell death in human breast cancer cells. Cancer Res 56: 2745-2747.
Postic, C., and J. Girard. 2008. Contribution of de novo fatty acid synthesis to hepatic steatosis and insulin resistance: lessons from genetically engineered mice. J Clin Invest 118: 829-838.
Queen, et al., Cell-type specific regulation of a kappa immunoglobulin gene by promoter and enhancer elements, Immunol. Rev. 89:49-68, (1986).
Samuel, V. T., K. F. Petersen, and G. I. Shulman. 2010. Lipid-induced insulin resistance: unravelling the mechanism. Lancet 375: 2267-2277.
Schäffler, A., A. Ehling, E. Neumann, H. Herfarth, G. Paul, I. Tarner, S. Gay, J. Scholmerich, and U. Muller-Ladner. 2003. Genomic organization, promoter, amino acid sequence, chromosomal localization, and expression of the human gene for CORS-26 (collagenous repeat-containing sequence of 26-kDa protein). Biochim Biophys Acta 1630: 123-129.
Seldin, M. M., J. M. Peterson, M. S. Byerly, Z. Wei, and G. W. Wong. 2012. Myonectin (CTRP15), a novel myokine that links skeletal muscle to systemic lipid homeostasis. J Biol Chem 287: 11968-11980.
Skinner et al., Use of the Glu-Glu-Ph-C-terminal epitope for rapid purification of the catalytic domain of normal and mutant ras GTPase-activating proteins, J. Biol. Chem., 266:15163-15166 (1991).
Szczepaniak, L. S., P. Nurenberg, D. Leonard, J. D. Browning, J. S. Reingold, S. Grundy, H. H. Hobbs, and R. L. Dobbins. 2005. Magnetic resonance spectroscopy to measure hepatic triglyceride content: prevalence of hepatic steatosis in the general population. Am J Physiol Endocrinol Metab 288: E462-468.
Sunny, N. E., E. J. Parks, J. D. Browning, and S. C. Burgess. 2011. Excessive hepatic mitochondrial TCA cycle and gluconeogenesis in humans with nonalcoholic fatty liver disease. Cell Metab 14: 804-810.
Takeuchi, K., and K. Reue. 2009. Biochemistry, physiology, and genetics of GPAT, AGPAT, and lipin enzymes in triglyceride synthesis. Am J Physiol Endocrinol Metab 296: E1195-1209.
Wu, J. W., S. P. Wang, F. Alvarez, S. Casavant, N. Gauthier, L. Abed, K. G. Soni, G. Yang, and G. A. Mitchell. 2011. Deficiency of liver adipose triglyceride lipase in mice causes progressive hepatic steatosis. Hepatology 54: 122-132.
Thompson J. D. et al., Clustal W: improving the sensitivity of progressive multiple sequence alignment through sequence weighting, postion-specific gap penalties and weight matrix choice, Nucleic Acids Res. 22:4673-4680 (1994).

(Continued)

*Primary Examiner* — Julie Ha
*Assistant Examiner* — Kristina M Hellman
(74) *Attorney, Agent, or Firm* — Michael Best & Friedrich LLP; Jeffrey W. Childers

(57) ABSTRACT

Methods are disclosed for treating or preventing fatty liver disease using a CTRP3 polypeptide or functional variant thereof.

8 Claims, 10 Drawing Sheets

(56) References Cited

OTHER PUBLICATIONS

Treeprasertsuk, S., S. Leverage, L. A. Adams, K. D. Lindor, J. St Sauver, and P. Angulo. 2012. The Framingham risk score and heart disease in nonalcoholic fatty liver disease. Liver Int 32: 945-950.
Utzschneider et al., Review: hte role of insulin resistance in nonalcoholic fatty liver disease, 2006, J. Clin. Endocrinol. Metab. 91:4753-4761.
Uysal, K. T., S. M. Wiesbrock, M. W. Marino, and G. S. Hotamisligil. 1997. Protection from obesity-induced insulin resistance in mice lacking TNF-alpha function. Nature 389: 610-614.
Wei, Z., X. Lei, M. M. Seldin, and G. W. Wong. 2012. Endopeptidase cleavage generates a functionally distinct isoform of C1q/tumor necrosis factor-related protein-12 (CTRP12) with an altered oligomeric state and signaling specificity. J Biol Chem 287: 35804-35814.
Wei, Z., J. M. Peterson, X. Lei, L. Cebotaru, M. J. Wolfgang, G. C. Baldeviano, and G. W. Wong. 2012. C1q/TNF-related protein-12 (CTRP12), a novel adipokine that improves insulin sensitivity and glycemic control in mouse models of obesity and diabetes. J Biol Chem 287: 10301-10315.
Wei, Z., J. M. Peterson, and G. W. Wong. 2011. Metabolic regulation by C1q/TNF-related protein-13 (CTRP13): activation of AMP-activated protein kinase and suppression of fatty acid-induced JNK signaling. J Biol Chem 286: 15652-15665.
Wolfing, B., C. Buechler, J. Weigert, M. Neumeier, C. Aslanidis, J. Schoelmerich, and A. Schaffler. 2008. Effects of the new C1q/TNF-related protein (CTRP-3) "cartonectin" on the adipocytic secretion of adipokines. Obesity (Silver Spring) 16: 1481-1486.
Wong, G. W., P. S. Foster, S. Yasuda, J. C. Qi, S. Mahalingam, E. A. Mellor, G. Katsoulotos, L. Li, J. A. Boyce, S. A. Krilis, and R. L. Stevens. 2002. Biochemical and functional characterization of human transmembrane tryptase (TMT)/tryptase gamma. TMT is an exocytosed mast cell protease that induces airway hyperresponsiveness in vivo via an interleukin-13/interleukin-4 receptor alpha/signal transducer and activator of transcription (STAT) 6-dependent pathway. J Biol Chem 277: 41906-41915.
Wong, G. W., S. A. Krawczyk, C. Kitidis-Mitrokostas, G. Ge, E. Spooner, C. Hug, R. Gimeno, and H. F. Lodish. 2009. Identification and characterization of CTRP9, a novel secreted glycoprotein, from adipose tissue that reduces serum glucose in mice and forms heterotrimers with adiponectin. FASEB J 23: 241-258.
Wong, G. W., S. A. Krawczyk, C. Kitidis-Mitrokostas, T. Revell, R. Gimeno, and H. F. Lodish. 2008. Molecular, biochemical and functional characterizations of C1q/TNF family members: adipose-tissue-selective expression patterns, regulation by PPAR-gamma agonist, cysteine-mediated oligomerizations, combinatorial associations and metabolic functions. Biochem J 416: 161-177.
Wong, G. W., J. Wang, C. Hug, T. S. Tsao, and H. F. Lodish. 2004. A family of Acrp30/adiponectin structural and functional paralogs. Proc Natl Acad Sci U S A 101: 10302-10307.
Akiyama, H., S. Furukawa, S. Wakisaka, and T. Maeda. 2006. Cartducin stimulates mesenchymal chondroprogenitor cell proliferation through both extracellular signal-regulated kinase and phosphatidylinositol 3-kinase/Akt pathways. Febs J 273: 2257-2263.
Akiyama, H., S. Furukawa, S. Wakisaka, and T. Maeda. 2007. CTRP3/cartducin promotes proliferation and migration of endothelial cells. Mol Cell Biochem 304: 243-248.
Akiyama, H., S. Furukawa, S. Wakisaka, and T. Maeda. 2009. Elevated expression of CTRP3/cartducin contributes to promotion of osteosarcoma cell proliferation. Oncol Rep 21: 1477-1481.
Xu, A., Y. Wang, H. Keshaw, L. Y. Xu, K. S. Lam, and G. J. Cooper. 2003. The fat-derived hormone adiponectin alleviates alcoholic and nonalcoholic fatty liver diseases in mice. J Clin Invest 112: 91-100.
Bell, R. M., and R. A. Coleman. 1980. Enzymes of glycerolipid synthesis in eukaryotes. Annu Rev Biochem 49: 459-487.
Brown, J. M., J. L. Betters, C. Lord, Y. Ma, X. Han, K. Yang, H. M. Alger, J. Melchior, J. Sawyer, R. Shah, M. D. Wilson, X. Liu, M. J. Graham, R. Lee, R. Crooke, G. I. Shulman, B. Xue, H. Shi, and L. Yu. 2010. CGI-58 knockdown in mice causes hepatic steatosis but prevents diet-induced obesity and glucose intolerance. J Lipid Res 51: 3306-3315.
Browning, J. D., and J. D. Horton. 2004. Molecular mediators of hepatic steatosis and liver injury. J Clin Invest 114: 147-152.
Buzzai, M., D. E. Bauer, R. G. Jones, R. J. Deberardinis, G. Hatzivassiliou, R. L. Elstrom, and C. B. Thompson. 2005. The glucose dependence of Akt-transformed cells can be reversed by pharmacologic activation of fatty acid beta-oxidation. Oncogene 24: 4165-4173.
Cao, J., Y. Zhou, H. Peng, X. Huang, S. Stahler, V. Suri, A. Qadri, T. Gareski, J. Jones, S. Hahm, M. Perreault, J. McKew, M. Shi, X. Xu, J. F. Tobin, and R. E. Gimeno. 2011. Targeting Acyl-CoA:diacylglycerol acyltransferase 1 (DGAT1) with small molecule inhibitors for the treatment of metabolic diseases. J Biol Chem 286: 41838-41851.
Chakravarthy, M. V., Z. Pan, Y. Zhu, K. Tordjman, J. G. Schneider, T. Coleman, J. Turk, and C. F. Semenkovich. 2005. "New" hepatic fat activates PPARalpha to maintain glucose, lipid, and cholesterol homeostasis. Cell Metab 1: 309-322.
Choi, C. S., D. B. Savage, A. Kulkarni, X. X. Yu, Z. X. Liu, K Morino, S. Kim, A. Distefano, V. T. Samuel, S. Neschen, D. Zhang, A. Wang, X. M. Zhang, M. Kahn, G. W. Cline, S. K. Pandey, J. G. Geisler, S. Bhanot, B. P. Monia, and G. I. Shulman. 2007. Suppression of diacylglycerol acyltransferase-2 (DGAT2), but not DGAT1, with antisense oligonucleotides reverses diet-induced hepatic steatosis and insulin resistance. J Biol Chem 282: 22678-22688.
Clark, The epidemiology of nonalcoholic fatty liver disease in adults, 2006, J. Clin. Gastroenterol. 40(Suppl 1):S5-S10.
Cohen, J. C., J. D. Horton, and H. H. Hobbs. 2011. Human fatty liver disease: old questions and new insights. Science 332:1519-1523.
Enomoto, T., K. Ohashi, R. Shibata, A. Higuchi, S. Maruyama, Y. Izumiya, K. Walsh, T. Murohara, and N. Ouchi. 2011. Adipolin/C1qdc2/CTRP12 functions as an adipokine that improves glucose metabolism. J Biol Chem 286: 34552-34558.
Evan et al., Isolation of monoclonal antibodies specific for human c-myc proto-oncogene product, Molecular and Cellular Biology, 5:3610-3616 (1985).
Fabian, M. A., W. H. Biggs, 3rd, D. K. Treiber, C. E. Atteridge, M. D. Azimioara, M. G. Benedetti, T. A. Carter, P. Ciceri, P. T. Edeen, M. Floyd, J. M. Ford, M. Galvin, J. L. Gerlach, R. M. Grotzfeld, S. Herrgard, D. E. Insko, M. A. Insko, A. G. Lai, J. M. Lelias, S. A. Mehta, Z. V. Milanov, A. M. Velasco, L. M. Wodicka, H. K. Patel, P. P. Zarrinkar, and D. J. Lockhart. 2005. A small molecule-kinase interaction map for clinical kinase inhibitors. Nat Biotechnol 23: 329-336.
Farese, R. V., Jr., R. Zechner, C. B. Newgard, and T. C. Walther. 2012. The problem of establishing relationships between hepatic steatosis and hepatic insulin resistance. Cell Metab 15: 570-573.
Fedorov, Y., E. M. Anderson, A. Birmingham, A. Reynolds, J. Karpilow, K. Robinson, D. Leake, W. S. Marshall, and A. Khvorova. 2006. Off-target effects by siRNA can induce toxic phenotype. RNA 12: 1188-1196.
Field et al., Purification of a ras-responsive adenylyl cyclase complex from s. cerevisiae by use of an eptiope addition method, Mol. Cell. Biol., 8:2159-2165 (1988).
Gregor, M. F., and G. S. Hotamisligil. 2011. Inflammatory mechanisms in obesity. Annu Rev Immunol 29: 415-445.
Hofmann, C., N. Chen, F. Obermeier, G. Paul, C. Buchler, A. Kopp, W. Falk, and A. Schaffler. 2011. C1q/TNF-related protein-3 (CTRP-3) is secreted by visceral adipose tissue and exerts antiinflammatory and antifibrotic effects in primary human colonic fibroblasts. Inflamm Bowel Dis 17: 2462-2471.
Yamauchi, T., J. Kamon, H. Waki, Y. Terauchi, N. Kubota, K. Hara, Y. Mori, T. Ide, K. Murakami, N. Tsuboyama-Kasaoka, O. Ezaki, Y. Akanuma, O. Gavrilova, C. Vinson, M. L. Reitman, H. Kagechika, K. Shudo, M. Yoda, Y. Nakano, K. Tobe, R. Nagai, S. Kimura, M. Tomita, P. Froguel, and T. Kadowaki. 2001. The fat-derived hormone adiponectin reverses insulin resistance associated with both lipoatrophy and obesity. Nat Med 7: 941-946.
Hotamisligil, G. S. 2006. Inflammation and metabolic disorders. Nature 444: 860-867.

(56) References Cited

OTHER PUBLICATIONS

Hoy, A. J., C. R. Bruce, S. M. Turpin, A. J. Morris, M. A. Febbraio, and M. J. Watt. 2011. Adipose triglyceride lipase-null mice are resistant to high-fat diet-induced insulin resistance despite reduced energy expenditure and ectopic lipid accumulation. Endocrinology 152: 48-58.
Jackson, A. L., J. Burchard, J. Schelter, B. N. Chau, M. Cleary, L. Lim, and P. S. Linsley. 2006. Widespread siRNA "off-target" transcript silencing mediated by seed region sequence complementarily. RNA 12: 1179-1187.
Jornayvaz, F. R., A. L. Birkenfeld, M. J. Jurczak, S. Kanda, B. A. Guigni, D. C. Jiang, D. Zhang, H. Y. Lee, V. T. Samuel, and G. I. Shulman. 2011. Hepatic insulin resistance in mice with hepatic overexpression of diacylglycerol acyltransferase 2. Proc Natl Acad Sci U S A 108: 5748-5752.
Kim, J. K., J. J. Fillmore, Y. Chen, C. Yu, I. K. Moore, M. Pypaert, E. P. Lutz, Y. Kako, W. Velez-Carrasco, I. J. Goldberg, J. L. Breslow, and G. I. Shulman. 2001. Tissue-specific overexpression of lipoprotein lipase causes tissue-specific insulin resistance. Proc Natl Acad Sci U S A 98: 7522-7527.
Kopp, A., M. Bala, C. Buechler, W. Falk, P. Gross, M. Neumeier, J. Scholmerich, and A. Schaffler. 2010. C1q/related protein-3 represents a novel and endogenous lipopolysaccharide antagonist of the adipose tissue. Endocrinology 151: 5267-5278.
Kopp, A., M. Bala, J. Weigert, C. Buchler, M. Neumeier, C. Aslanidis, J. Scholmerich, and A. Schaffler. 2010. Effects of the new adiponectin paralogous protein CTRP-3 and of LPS on cytokine release from monocytes of patients with type 2 diabetes mellitus. Cytokine 49: 51-57.
Kotronen, A., A. Seppala-Lindroos, R. Bergholm, and H. Yki-Jarvinen. 2008. Tissue specificity of insulin resistance in humans: fat in the liver rather than muscle is associated with features of the metabolic syndrome. Diabetologia 51: 130-138.
Kotronen, A., S. Vehkavaara, A. Seppala-Lindroos, R. Bergholm, and H. Yki-Jarvinen. 2007. Effect of liver fat on insulin clearance. Am J Physiol Endocrinol Metab 293: E1709-1715.
Kuhajda, F. P., S. Aja, Y. Tu, W. F. Han, S. M. Medghalchi, R. El Meskini, L. E. Landree, J. M. Peterson, K. Daniels, K. Wong, E. A. Wydysh, C. A. Townsend, and G. V. Ronnett. 2011. Pharmacological glycerol-3-phosphate acyltransferase inhibition decreases food intake and adiposity and increases insulin sensitivity in diet-induced obesity, Am J Physiol Regul Integr Comp Physiol 301: R116-130.
Lazo, M., and J. M. Clark. 2008. The epidemiology of nonalcoholic fatty liver disease: a global perspective. Semin Liver Dis 28: 339-350.
Listenberger, L. L., D. S. Ory, and J. E. Schaffer. 2001. Palmitate-induced apoptosis can occur through a ceramide-independent pathway. J Biol Chem 276: 14890-14895.
Lutz-Freyermuth et al., Quantitative determination that one of two potential RNA-binding domains of the A protein component of the U1 small nuclear ribonucleoprotein complex binds with high affinity to stem-loop II of U1 RNA, Proc. Natl. Acad. Sci. USA, 87:6393-6397 (1990).
Luyckx, F. H., C. Desaive, A. Thiry, W. Dewe, A. J. Scheen, J. E. Gielen, and P. J. Lefebvre. 1998. Liver abnormalities in severely obese subjects: effect of drastic weight loss after gastroplasty. Int J Obes Relat Metab Disord 22: 222-226.
Maeda, T., M. Abe, K. Kurisu, A. Jikko, and S. Furukawa. 2001. Molecular cloning and characterization of a novel gene, CORS26, encoding a putative secretory protein and its possible involvement in skeletal development. J Biol Chem 276: 3628-3634.
Maeda, T., A. Jikko, M. Abe, T. Yokohama-Tamaki, H. Akiyama, S. Furukawa, M. Takigawa, and S. Wakisaka. 2006. Cartducin, a paralog of Acrp30/adiponectin, is induced during chondrogenic differentiation and promotes proliferation of chondrogenic precursors and chondrocytes. J Cell Physiol 206: 537-544.

Maeda, T., and S. Wakisaka. 2010. CTRP3/cartducin is induced by transforming growth factor-betal and promotes vascular smooth muscle cell proliferation. Cell Biol Int 34: 261-266.
Yen, C. L., S. J. Stone, S. Koliwad, C. Harris, and R. V. Farese, Jr. 2008. Thematic review series: glycerolipids. DGAT enzymes and triacylglycerol biosynthesis. J Lipid Res 49: 2283-2301.
Millar, J. S., D. A. Cromley, M. G. McCoy, D. J. Rader, and J. T. Billheimer. 2005. Determining hepatic triglyceride production in mice: comparison of poloxamer 407 with Triton WR-1339. J Lipid Res 46: 2023-2028.
Minehira, K., S. G. Young, C. J. Villanueva, L. Yetukuri, M. Oresic, M. K. Hellerstein, R. V. Farese, Jr., J. D. Horton, F. Preitner, B. Thorens, and L. Tappy. 2008. Blocking VLDL secretion causes hepatic steatosis but does not affect peripheral lipid stores or insulin sensitivity in mice. J Lipid Res 49: 2038-2044.
Monetti, M., M. C. Levin, M. J. Watt, M. P. Sajan, S. Marmor, B. K. Hubbard, R. D. Stevens, J. R. Bain, C. B. Newgard, R. V. Farese, Sr., A. L. Hevener, and R. V. Farese, Jr. 2007. Dissociation of hepatic steatosis and insulin resistance in mice overexpressing DGAT in the liver. Cell Metab 6: 69-78.
Monsenego, J., A. Mansouri, M. Akkaoui, V. Lenoir, C. Esnous, V. Fauveau, V. Tavernier, J. Girard, and C. Prip-Buus. 2011. Enhancing liver mitochondrial fatty acid oxidation capacity in obese mice improves insulin sensitivity independently of hepatic steatosis. J Hepatol 56: 632-639.
Nagle, C. A., E. L. Klett, and R. A. Coleman. 2009. Hepatic triacylglycerol accumulation and insulin resistance. J Lipid Res 50 Suppl: S74-79.
Yi, W., Y. Sun, Y. Yuan, W. B. Lau, Q. Zheng, X. Wang, Y. Wang, X. Shang, E. Gao, W. J. Koch, and X. L. Ma. 2012. C1g/tumor necrosis factor-related protein-3, a newly identified adipokine, is a novel antiapoptotic, proangiogenic, and cardioprotective molecule in the ischemic mouse heart. Circulation 125: 3159-3169.
Niwa, H., K. Yamamura, and J. Miyazaki. 1991. Efficient selection for high-expression transfectants with a novel eukaryotic vector. Gene 108: 193-199.
Paborsky et al., Mammalian cell transient expression of tissue factor for hte production of antigen, Protein Engineering, 3(6):547-553 (1990).
Peterson, J. M., S. Aja, Z. Wei, and G. W. Wong. 2012. C1q/TNF-related protein-1 (CTRP1) enhances fatty acid oxidation via AMPK activation and ACC inhibition. J Biol Chem 287: 1576-1587.
Petersen, K. F., S. Dufour, D. Befroy, M. Lehrke, R. E. Hendler, and G. I. Shulman. 2005. Reversal of nonalcoholic hepatic steatosis, hepatic insulin resistance, and hyperglycemia by moderate weight reduction in patients with type 2 diabetes. Diabetes 54: 603-608.
International Search Report and Written Opinion dated Jun. 16, 2014 from related PCT Patent Application No. PCT/US2014/24193.
Peterson et al., C1q/TNF-related protein-3 (CTRP3), a novel adipokine that regulates 1-20 hepatic glucose output. J Biol Chem. Dec. 17, 2010; 285(51):39691-701.
C1QT3_HUMAN, UniprotKB Accession No. Q9BXJ4, Complement C1q tumor necrosis factor—1-20 related protein 3, Nov. 28, 2012 [online]. [Retrieved on May 20, 2014]. Retrieved from the internet <URL: http://www.ncbi.nlm.nih.gov/protein/201778657sat=16&satkey"15075667>.
Parekh et al., Abnormal lipid and glucose metabolism in obesity: implications for nonalcoholic fatty liver disease. Gastroenterology. May 2007;132(6):2191-207.
Yoo et al., Implication of progranulin and C1q/TNF-related protein-3 (CTRP3) on inflammation and atherosclerosis in subjects with or without metabolic syndrome. PLoS One, Feb. 2013; 8(2):e55744.
Peterson et al. "CTRP3 attenuates diet-induced hepatic steatosis by regulating triglyceride metabolism" American Journal of Physiology—Gastrointestinal and Liver Physiology 305: G214-G224, Jun. 6, 2013.

\* cited by examiner

*A*

MLWRQLIYWQLLALFFLPFCLCQDEYMESPQTGGLPPDCSKCCHGDYSFRGYQGPPGPPGPPGIPGNHGNNGNNGATGH
EGAKGEKGDKGDLGPRGERGQHGPKGEKGYPGIPPELQIAFMASLATHFSNQNSGIIFSSVETNIGNFFDVMTGRFGAP
VSGVYFFTFSMMKHEDVEEVYVYLMHNGNTVFSMYSYEMKGKSDTSSNHAVLKLAKGDEVWLRMGNGALHGDHQRFSTF
AGF (SEQ ID NO:1)

*B* agccttatttattacacaccaaagtataaaaccactccgccgctgcagctctcagctccagtcctggcatctgcccgag
gagaccacgctcctggagctctgctgtcttctcagggagactctgaggctctgttgagaatcatgctttggaggcagct
catctattggcaactgctggctttgttttcctcctttttgcctgtgtcaagatgaatacatggagtctccacaaacc
ggaggactaccccagactgcagtaagtgttgtcatggagactacagctttcgaggctaccaaggcccccctgggccac
cgggccctcctggcattccaggaaaccatggaaacaatggcaacaatggagccactggtcatgaaggagccaaaggtga
gaagggcgacaaaggtgacctggggcctcgaggggagcggggggcagcatggccccaaaggagagaagggctacccgggg
attccaccagaacttcagattgcattcatggcttctctggcaacccacttcagcaatcagaacagtgggattatcttca
gcagtgttgagaccaacattggaaacttcttttgatgtcatgactggtagatttggggcccagtatcaggtgtgtattt
cttcaccttcagcatgatgaagcatgaggatgttgaggaagtgtatgtgtaccttatgcacaatggcaacacagtcttc
agcatgtacagctatgaaatgaagggcaaatcagatacatccagcaatcatgctgtgctgaagctagccaaaggggatg
aggtttggctgcgaatgggcaatggcgctctccatggggaccaccaacgcttctccacctttgcaggattcctgctctt
tgaaactaagtaaatatatgactagaatagctccactttggggaagacttgtagctgagctgatttgttacgatctgag
gaacattaaagttgagggttttacattgctgtattcaaaaaattattggttgcaatgttgttcacgctacaggtacacc
aataatgttggacaattcaggggctcagaagaatcaaccacaaaatagtcttctcagatgaccttgactaatatactca
gcatctttatcactctttccttggcacctaaaagataattctcctctgacgcaggttggaaatatttttttctatcaca
gaagtcatttgcaaagaattttgactactctgcttttaatttaataccagttttcaggaacccctgaagttttaagttc
attattctttataacatttgagagaatcggatgtagtgatatgacagggctggggcaagaacaggggcactagctgcct
tattagctaatttagtgccctccgtgttcagcttagcctttgacccttttccttttgatccacaaaatacattaaaactc
tgaattcacatacaatgctattttaaagtcaatagattttagctataaagtgcttgaccagtaatgtggttgtaattt
gtgtatgttcccccacatcgcccccaacttcggatgtggggtcaggaggttgaggttcactattaacaaatgtcataaa
tatctcatagaggtacagtgccaatagatattcaaatgttgcatgttgaccagagggatttttatatctgaagaacatac
actattaataaatacccttagagaaagattttgacctggctttagataaaactgtggcaagaaaaatgtaatgagcaata
tatggaaataaacacaccctttgttaaagatactttctaaacttgtgtttaataaacttaatagtcatagaattgtaaa
tcactatggttaacagaaagtgaaaatattttcatgcagatgatgtgaacagccatgtgaataggtgacttgggcacac
agcagggtcatatgacttcagaaaacttcgcttttcagttattccattgttataatgtcaacccttaagacattgatg
tttagagggctcacaaataaaatctgaatacctgtaaggaaagaggttttttatcacataccttaagtctttgtaatgt
tcatgcttaaattctaagttttcaccttagtgacacacaaggtttggttgtaggcaacaagtcccaggtgtgtgggaaa
ttgattcacaacagagatgggaaaaggtgcagataatttccaatgccttcacaatttacccatgaccagaaatatactt
ggaagactgatttcacaagtgtcccaaaactgagatgctaaaaaggaaacagtaggtaggtgtcataggaaatttacat
gtaccatctaataaacaaacttgcaaattctaaatctttttttttttgagacagtttcacgctgctgcccaggctgga
gtgcagtggcatgatctcagctcaccgcagcctccgcctcctgggttcaagtgactctcctacctcagcctcctgagta
gctgggactacaggcgcccaccaccaggaccagctaatttttaatgtttctaatagagatggggtttcaccatgttgac
caggccggtctgaactcctgacctcaggtgatctgcctgcctcggtcttccaaagtgctgggattacaggcgtgagcc
cccgcacccagccgcaaattctaaatcttaaaacaactctgcaaacgaagcacttgagtttctgcttgcttcagggatg
taatatggtgtagaactgtttcacataatgatcagccttggtaattttccagtgtagaaaacattatatttgacccttg
gacaacaaagagattatattgaaggaatttttattgattgtatcatgaataaaagctgaagtcaaaattaaaatgtaaaa
aaataattcagaggatggaatatgcaaatgtaaactccaaatgatgtggctggaattcataaacatttactttatgcaa
gatactgtgctattccaggcactcctatggcatttaaagtacaattcttaccttccctaatttttcaacctagtagagg
acaataggctaaagggaataagtacatggataacaaaacataaagtagaatgttttttacagccatagaaggcaaagggc
taggaattcacaggagagagaaacagtatctagctgagagcataagaaaagcttgtggaaaagataatatctgatgcc
agagacaatttcttgctttggtatgtttgaagtgttatatttaaatatatatatttttatttaaaaaactcactataga
aaatttataaaattccccaaaatatttagtataaaattaatcatcccatcaaatatttaaataatattactattttaaag
tgttttatttcagtctttttcctgcatgtatttatggcttttattttttaaatatagtaataaaataatttgaaattagctt
tttatatatttttgtatcttgctctaatgggttggactaaacatattaagaacactctcaaatgctactaaggacaatt
tgaaaacataattttaatgactgcataatttatttaacttcctgttttggaaaatatatttttttttttattacaaat
aatatgtcatgagcattctcttttaaaaaaataaactatgtgtgcatataaaaaaaaaaaaaaaaaa (SEQ ID
NO:2)

MLWRQLIYWQLLALFFLPFCLCQDEYMEVSGRTNKVVARIVQSHQQTGRSGSRREKVRERSHPKTGTVDNNTSTDLKSL
RPDELPHPEVDDLAQITTFWGQSPQTGGLPPDCSKCCHGDYSFRGYQGPPGPPGPPGIPGNHGNNGNNGATGHEGAKGE
KGDKGDLGPRGERGQHGPKGEKGYPGIPPELQIAFMASLATHFSNQNSGIIFSSVETNIGNFFDVMTGRFGAPVSGVYF
FTFSMMKHEDVEEVYVYLMHNGNTVFSMYSYEMKGKSDTSSNHAVLKLAKGDEVWLRMGNGALHGDHQRFSTFAGFLLF
ETK (SEQ ID NO:3)

B

```
agccttatttattacacaccaaagtataaaaccactccgccgctgcagctctcagctccagtcctggcatctgcccgag
gagaccacgctcctggagctctgctgtcttctcagggagactctgaggctctgttgagaatcatgctttggaggcagct
catctattggcaactgctggctttgttttcctccttttgcctgtgtcaagatgaatacatggaggtgagcggaaga
actaataaagtggtggcaagaatagtgcaaagccaccagcagactggccgtagcggctccaggaggagaaagtgagag
agcggagccatcctaaaactggactgtggataataacacttctacagacctaaaatccctgagaccagatgagctacc
gcaccccgaggtagatgacctagcccagatcaccacattctggggccagtctccacaaaccggaggactaccccagac
tgcagtaagtgttgtcatggagactacagctttcgaggctaccaaggccccctgggccaccgggcctcctggcattc
caggaaaccatggaaacaatggcaacaatggagccactggtcatgaaggagccaaaggtgagaagggcgacaaaggtga
cctgggggcctcgaggggagcggggcagcatggccccaaggagagaagggctacccggggattccaccagaacttcag
attgcattcatggcttctctggcaacccacttcagcaatcagaacagtgggattatcttcagcagtgttgagaccaaca
ttggaaacttctttgatgtcatgactggtagatttggggccccagtatcaggtgtgtatttcttccacttcagcatgat
gaagcatgaggatgttgaggaagtgtatgtgtaccttatgcacaatggcaacacagtcttcagcatgtacagctatgaa
atgaagggcaaatcagatacatccagcaatcatgctgtgctgaagctagccaaaggggatgaggtttggctgcgaatgg
gcaatggcgctctccatggggaccaccaacgcttctccaccttggcaggattcctgctctttgaaactaagtaaatata
tgactagaatagctccactttggggaagacttgtagctgagctgatttgttacgatctgaggaacattaaagttgaggg
ttttacattgctgtattcaaaaaattattggttgcaatgttgttcacgctacaggtacaccaataatgttggacaattc
agggctcagaagaatcaaccacaaaatagtcttctcagatgaccttgactaatatactcagcatctttatcactctt
ccttggcacctaaaagataattctcctctgacgcaggttggaaatatttttttctatcacagaagtcatttgcaaagaa
tttgactactctgcttttaatttaataccagttttcaggaaccccctgaagttttaagttcattattcttttataacatt
tgagagaatcggatgtagtgatatgacagggctggggcaagaacagggggcactagctgccttattagctaatttagtgc
cctccgtgttcagcttagcctttgacccttttccttttgatccacaaaatacattaaaactctgaattcacatacaatgc
tattttaaagtcaatagattttagctataaagtgcttgaccagtaatgtggttgtaattttgtgtatgttccccacat
cgcccccaacttcggatgtggggtcaggaggttgaggttcactattaacaaatgtcataaatatctcatagaggtacag
tgccaatagatattcaaatgttgcatgttgaccagagggattttatatctgaagaacatacactattaataaataccttc
agagaaagattttgacctggcttagataaaactgtggcaagaaaaatgtaatgagcaatatatggaaataaacacacc
tttgttaaagatactttctaaacttgtgtttaataaactttaatagtcatagaattgtaaatcactatggttaacagaa
agtgaaaatattttcatgcagatgatgtgaacagccatgtgaataggtgacttgggcacacagcagggtcatatgactt
cagaaaacttcgcttttcagttattccattgttataatgtcaaccctttaagacattgatgtttagagggctcacaaat
aaaatctgaatacctgtaaggaaagaggtttttatcacataccttaagtctttgtaatgttcatgcttaaattctaag
ttttcaccttagtgacacacaaggtttggttgtaggcaacaagtcccaggtgtgtgggaaattgattcacaacagagat
gggaaaaggtgcagataatttccaatgccttcacaatttacccatgaccagaaatatacttggaagactgatttcacaa
gtgtcccaaaactgagatgctaaaaaggaaacagtaggtaggtgtcataggaaatttacatgtaccatctaataaacaa
acttgcaaattctaaatcttttttttttttgagacagtttcacgctgctgcccaggctggagtgcagtggcatgatctc
agctcaccgcagcctccgcctcctgggttcaagtgactctcctacctcagcctcctgagtagctgggactacaggcgcc
caccaccaggaccagctaatttttaatgtttctaatagaagtgggggttttccaccatgttgaccaggccggtctggaactc
ctgacctcaggtgatctgcctgcctcggtcttccaaagtgctgggattacaggcgtgagccccgcacccagccgcaaa
ttctaaatcttaaaacaactctgcaaacgaagcacttgagtttctgcttgcttcagggatgtaatatggtgtagaactg
tttcacataatgatcagccttggtaattttccagtgtagaaaacattatatttgacccttggacaacaaagagattata
ttgaaggaatttttattgattgtatcatgaataaaagctgaagtcaaaattaaaatgtaaaaaataattcagaggatgg
aatatgcaaatgtaaactccaaatgatgtggctggaattcataaacatttactttatgcaagatactgtgctattccag
gcactcctatggcatttaaagtacaattcttaccttccctaattttcaacctagtagaggacaataggctaaaggggaa
taagtacatggataacaaaacataaagtagaatgttttacagccatagaaggcaaagggctaggaattcacaggagag
agaaacagtatctagctgagagcataagaaaagcttgtggaaaagataatatctgatggccagagacaatttcttgctt
tggtatgtttgaagtgttatatttaaatatatatatttttatttaaaaaactcactatagaaaatttataaaattcccc
aaaatatttagtataaaattaatcatcccatcaaatattaataatattactattttaaagtgtttatttcagtcttttt
cctgcatgtatttatggcttttatttttaaatatagtaataaaataatttgaaattagcttttatatattttgtatc
ttgctctaatgggttggactaaacatattaagaacactctcaaatgctactaaggacaatttgaaaacataatttttaat
gactgcataatttatttaactttcctgttttggaaaatattattttttttattacaaataatatgtcatgagcattc
tcttttttaaaaaaataaactatgtgtgcatataaaaaaaaaaaaaaaaaa (SEQ ID NO:4)
```

*Fig. 2*

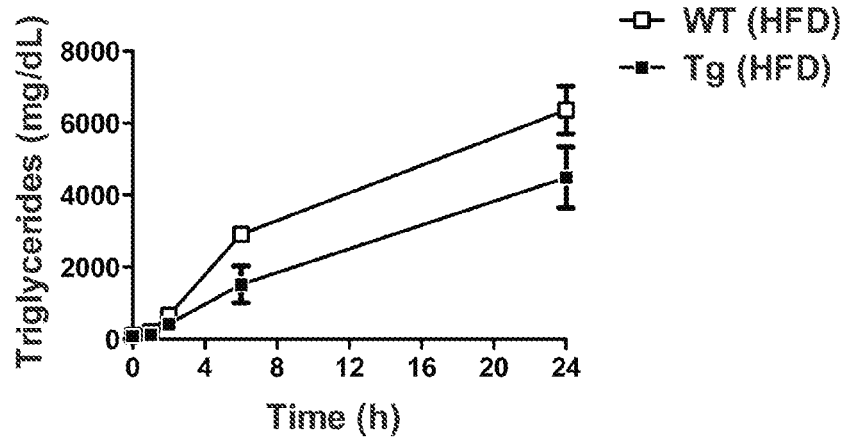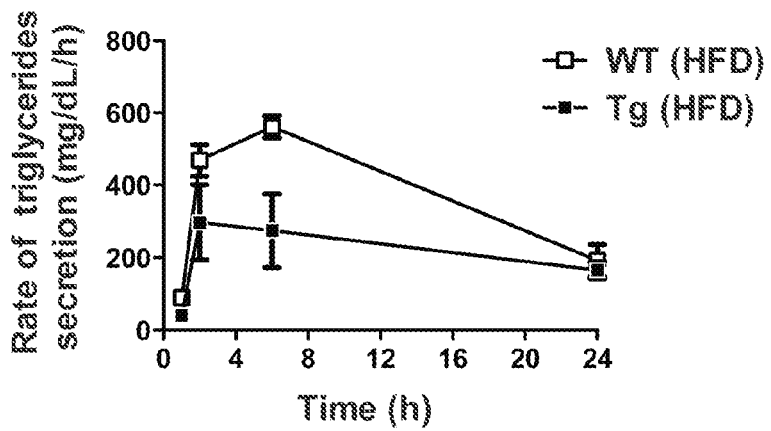
Fig. 7

SEQUENCE LISTING

```
<160> NUMBER OF SEQ ID NOS: 45

<210> SEQ ID NO 1
<211> LENGTH: 240
<212> TYPE: PRT
<213> ORGANISM: Homo sapiens

<400> SEQUENCE: 1

Met Leu Trp Arg Gln Leu Ile Tyr Trp Gln Leu Leu Ala Leu Phe Phe
1               5                   10                  15

Leu Pro Phe Cys Leu Cys Gln Asp Glu Tyr Met Glu Ser Pro Gln Thr
            20                  25                  30

Gly Gly Leu Pro Pro Asp Cys Ser Lys Cys Cys His Gly Asp Tyr Ser
        35                  40                  45

Phe Arg Gly Tyr Gln Gly Pro Pro Gly Pro Pro Gly Pro Pro Gly Ile
    50                  55                  60

Pro Gly Asn His Gly Asn Asn Gly Asn Asn Gly Ala Thr Gly His Glu
65                  70                  75                  80

Gly Ala Lys Gly Glu Lys Gly Asp Lys Gly Asp Leu Gly Pro Arg Gly
                85                  90                  95

Glu Arg Gly Gln His Gly Pro Lys Gly Glu Lys Gly Tyr Pro Gly Ile
            100                 105                 110

Pro Pro Glu Leu Gln Ile Ala Phe Met Ala Ser Leu Ala Thr His Phe
        115                 120                 125

Ser Asn Gln Asn Ser Gly Ile Ile Phe Ser Ser Val Glu Thr Asn Ile
    130                 135                 140

Gly Asn Phe Phe Asp Val Met Thr Gly Arg Phe Gly Ala Pro Val Ser
145                 150                 155                 160

Gly Val Tyr Phe Phe Thr Phe Ser Met Met Lys His Glu Asp Val Glu
                165                 170                 175
```

```
Glu Val Tyr Val Tyr Leu Met His Asn Gly Asn Thr Val Phe Ser Met
            180                 185                 190

Tyr Ser Tyr Glu Met Lys Gly Lys Ser Asp Thr Ser Ser Asn His Ala
        195                 200                 205

Val Leu Lys Leu Ala Lys Gly Asp Glu Val Trp Leu Arg Met Gly Asn
        210                 215                 220

Gly Ala Leu His Gly Asp His Gln Arg Phe Ser Thr Phe Ala Gly Phe
225                 230                 235                 240

<210> SEQ ID NO 2
<211> LENGTH: 3624
<212> TYPE: DNA
<213> ORGANISM: Homo sapiens

<400> SEQUENCE: 2
```

| | | | | | |
|---|---|---|---|---|---|
| agccttattt | attacacacc | aaagtataaa | accactccgc | cgctgcagct | ctcagctcca | 60 |
| gtcctggcat | ctgcccgagg | agaccacgct | cctggagctc | tgctgtcttc | tcagggagac | 120 |
| tctgaggctc | tgttgagaat | catgcttggg | aggcagctca | tctattggca | actgctggct | 180 |
| ttgttttttcc | tccctttttg | cctgtgtcaa | gatgaataca | tggagtctcc | acaaaccgga | 240 |
| ggactacccc | cagactgcag | taagtgttgt | catggagact | acagctttcg | aggctaccaa | 300 |
| ggccccctg | ggccaccggg | ccctcctggc | attccaggaa | accatggaaa | caatggcaac | 360 |
| aatggagcca | ctggtcatga | aggagccaaa | ggtgagaagg | cgacaaagg | tgacctgggg | 420 |
| cctcgagggg | agcggggca | gcatggcccc | aaggagaga | agggctaccc | ggggattcca | 480 |
| ccagaacttc | agattgcatt | catggcttct | ctggcaaccc | acttcagcaa | tcagaacagt | 540 |
| gggattatct | tcagcagtgt | tgagaccaac | attggaaact | tctttgatgt | catgactggt | 600 |
| agatttgggg | ccccagtatc | aggtgtgtat | tcttcaccct | tcagcatgat | gaagcatgag | 660 |
| gatgttgagg | aagtgtatgt | gtaccttatg | cacaatggca | acacagtctt | cagcatgtac | 720 |
| agctatgaaa | tgaagggcaa | atcagataca | tccagcaatc | atgctgtgct | gaagctagcc | 780 |
| aaaggggatg | aggtttggct | gcgaatgggc | aatggcgctc | tccatgggga | ccaccaacgc | 840 |
| ttctccacct | ttgcaggatt | cctgctcttt | gaaactaagt | aaatatatga | ctagaatagc | 900 |
| tccactttgg | ggaagacttg | tagctgagct | gatttgttac | gatctgagga | acattaaagt | 960 |
| tgagggtttt | acattgctgt | attcaaaaaa | ttattggttg | caatgttgtt | cacgctacag | 1020 |
| gtacaccaat | aatgttggac | aattcagggg | ctcagaagaa | tcaaccacaa | aatagtcttc | 1080 |
| tcagatgacc | ttgactaata | tactcagcat | ctttatcact | ctttccttgg | cacctaaaag | 1140 |
| ataattctcc | tctgacgcag | gttggaaata | tttttttcta | tcacagaagt | catttgcaaa | 1200 |
| gaattttgac | tactctgctt | ttaatttaat | accagttttc | aggaaccct | gaagttttaa | 1260 |
| gttcattatt | ctttataaca | tttgagagaa | tcggatgtag | tgatatgaca | gggctggggc | 1320 |
| aagaacaggg | gcactagctg | ccttattagc | taatttagtg | ccctccgtgt | tcagcttagc | 1380 |
| ctttgacccct | ttccttttga | tccacaaaat | acattaaaac | tctgaattca | catacaatgc | 1440 |
| tattttaaag | tcaatagatt | ttagctataa | agtgcttgac | cagtaatgtg | ttgtaatttt | 1500 |
| tgtgtatgtt | cccccacatc | gcccccaact | tcggatgtgg | ggtcaggagg | ttgaggttca | 1560 |
| ctattaacaa | atgtcataaa | tatctcatag | aggtacagtg | ccaatagata | ttcaaatgtt | 1620 |
| gcatgttgac | cagagggatt | ttatatctga | agaacataca | ctattaataa | ataccttaga | 1680 |
| gaaagatttt | gacctggctt | tagataaaac | tgtggcaaga | aaaatgtaat | gagcaatata | 1740 |
| tggaaataaa | cacacctttg | ttaaagatac | tttctaaact | tgtgtttaat | aaactttaat | 1800 |

```
agtcatagaa ttgtaaatca ctatggttaa cagaaagtga aaatattttc atgcagatga    1860
tgtgaacagc catgtgaata ggtgacttgg gcacacagca gggtcatatg acttcagaaa    1920
acttcgcttt tcagttattc cattgttata atgtcaaccc tttaagacat tgatgtttag    1980
agggctcaca aataaaatct gaatacctgt aaggaaagag gttttttatc atataccttc    2040
agtctttgta atgttcatgc ttaaattcta agttttcacc ttagtgacac acaaggtttg    2100
gttgtaggca acaagtccca ggtgtgtggg aaattgattc acaacagaga tgggaaaagg    2160
tgcagataat ttccaatgcc ttcacaattt acccatgacc agaaatatac ttggaagact    2220
gatttcacaa gtgtcccaaa actgagatgc taaaaaggaa acagtaggta ggtgtcatag    2280
gaaatttaca tgtaccatct aataaacaaa cttgcaaatt ctaaatcttt ttttttttg    2340 agacagtttc acgctgctgc ccaggctgga gtgcagtggc atgatctcag ctcaccgcag    2400
cctccgcctc ctgggttcaa gtgactctcc tacctcagcc tcctgagtag ctgggactac    2460
aggcgcccac caccaggacc agctaatttt taatgtttct aatagagatg gggtttcacc    2520
atgttgacca ggccggtctg gaactcctga cctcaggtga tctgcctgcc tcggtcttcc    2580
aaagtgctgg gattacaggc gtgagccccc gcacccagcc gcaaattcta aatcttaaaa    2640
caactctgca aacgaagcac ttgagtttct gcttgcttca gggatgtaat atggtgtaga    2700
actgtttcac ataatgatca gccttggtaa ttttccagtg tagaaaacat tatatttgac    2760
ccttggacaa caaagagatt atattgaagg aattttattg attgtatcat gaataaaagc    2820
tgaagtcaaa attaaaatgt aaaaaaataa ttcagaggat ggaatatgca aatgtaaact    2880
ccaaatgatg tggctggaat tcataaacat ttactttatg caagatactg tgctattcca    2940
ggcactccta tggcatttaa agtacaattc ttaccttccc taatttttca acctagtaga    3000
ggacaatagg ctaaagggaa taagtacatg gataacaaaa cataaagtag aatgttttta    3060
cagccataga aggcaaaggg ctaggaattc acaggagaga gaaacagtat ctagctgaga    3120
gcataagaaa agcttgtgga aaagataata tctgatggcc agagacaatt tcttgctttg    3180
gtatgtttga agtgttatat ttaaatatat atatttttat ttaaaaaact cactatagaa    3240
aatttataaa attccccaaa atatttagta taaaattaat catcccatca aatattaaat    3300
aatattacta ttttaaagtg tttatttcag tcttttcctg catgtattta tggcttttat    3360
ttttaaatat agtaataaaa taatttgaaa ttagcttttt atatattttt gtatcttgct    3420
ctaatgggtt ggactaaaca tattaagaac actctcaaat gctactaagg acaatttgaa    3480
aacataattt taatgactgc ataatttatt taactttcct gttttggaaa atattatttt    3540
tttttattta caaataatat gtcatgagca ttctcttttt aaaaaaataa actatgtgtg    3600
catataaaaa aaaaaaaaaa aaaa                                          3624
```

<210> SEQ ID NO 3
<211> LENGTH: 319
<212> TYPE: PRT
<213> ORGANISM: Homo sapiens

<400> SEQUENCE: 3

```
Met Leu Trp Arg Gln Leu Ile Tyr Trp Gln Leu Leu Ala Leu Phe Phe
1               5                   10                  15

Leu Pro Phe Cys Leu Cys Gln Asp Glu Tyr Met Glu Val Ser Gly Arg
            20                  25                  30

Thr Asn Lys Val Val Ala Arg Ile Val Gln Ser His Gln Gln Thr Gly
        35                  40                  45
```

```
Arg Ser Gly Ser Arg Arg Glu Lys Val Arg Glu Arg Ser His Pro Lys
 50                  55                  60

Thr Gly Thr Val Asp Asn Asn Thr Ser Thr Asp Leu Lys Ser Leu Arg
 65                  70                  75                  80

Pro Asp Glu Leu Pro His Pro Glu Val Asp Leu Ala Gln Ile Thr
                 85                  90                  95

Thr Phe Trp Gly Gln Ser Pro Gln Thr Gly Gly Leu Pro Pro Asp Cys
                100                 105                 110

Ser Lys Cys Cys His Gly Asp Tyr Ser Phe Arg Gly Tyr Gln Gly Pro
                115                 120                 125

Pro Gly Pro Pro Gly Pro Pro Gly Ile Pro Gly Asn His Gly Asn Asn
            130                 135                 140

Gly Asn Asn Gly Ala Thr Gly His Glu Gly Ala Lys Gly Glu Lys Gly
145                 150                 155                 160

Asp Lys Gly Asp Leu Gly Pro Arg Gly Glu Arg Gly Gln His Gly Pro
                165                 170                 175

Lys Gly Glu Lys Gly Tyr Pro Gly Ile Pro Pro Glu Leu Gln Ile Ala
                180                 185                 190

Phe Met Ala Ser Leu Ala Thr His Phe Ser Asn Gln Asn Ser Gly Ile
            195                 200                 205

Ile Phe Ser Ser Val Glu Thr Asn Ile Gly Asn Phe Phe Asp Val Met
210                 215                 220

Thr Gly Arg Phe Gly Ala Pro Val Ser Gly Val Tyr Phe Phe Thr Phe
225                 230                 235                 240

Ser Met Met Lys His Glu Asp Val Glu Glu Val Tyr Val Tyr Leu Met
                245                 250                 255

His Asn Gly Asn Thr Val Phe Ser Met Tyr Ser Tyr Glu Met Lys Gly
                260                 265                 270

Lys Ser Asp Thr Ser Ser Asn His Ala Val Leu Lys Leu Ala Lys Gly
            275                 280                 285

Asp Glu Val Trp Leu Arg Met Gly Asn Gly Ala Leu His Gly Asp His
            290                 295                 300

Gln Arg Phe Ser Thr Phe Ala Gly Phe Leu Leu Phe Glu Thr Lys
305                 310                 315

<210> SEQ ID NO 4
<211> LENGTH: 3843
<212> TYPE: DNA
<213> ORGANISM: Homo sapiens

<400> SEQUENCE: 4
agccttattt attacacacc aaagtataaa accactccgc cgctgcagct ctcagctcca      60
gtcctggcat ctgcccgagg agaccacgct cctggagctc tgctgtcttc tcagggagac     120
tctgaggctc tgttgagaat catgctttgg aggcagctca tctattggca actgctggct     180 ttgttttttcc tccctttttg cctgtgtcaa gatgaataca tggaggtgag cggaagaact     240
aataaagtgg tggcaagaat agtgcaaagc caccagcaga ctggccgtag cggctccagg     300
agggagaaag tgagagagcg gagccatcct aaaactggga ctgtggataa taacacttct     360
acagacctaa atccctgag accagatgag ctaccgcacc ccgaggtaga tgacctagcc     420
cagatcacca cattctgggg ccagtctcca caaaccggag gactaccccc agactgcagt     480
aagtgttgtc atggagacta cagctttcga ggctaccaag gcccccctgg ccaccgggc     540 cctcctggca ttccaggaaa ccatggaaac aatggcaaca atggagccac tggtcatgaa     600
```

```
ggagccaaag gtgagaaggg cgacaaaggt gacctggggc ctcgagggga gcggggcag      660 catggcccca aggagagaa gggctacccg gggattccac cagaacttca gattgcattc      720
atggcttctc tggcaaccca cttcagcaat cagaacagtg ggattatctt cagcagtgtt      780
gagaccaaca ttgaaaactt cttttgatgtc atgactggta gatttgggc cccagtatca      840 ggtgtgtatt tcttcacctt cagcatgatg aagcatgagg atgttgagga agtgtatgtg      900
taccttatgc acaatggcaa cacagtcttc agcatgtaca gctatgaaat gaagggcaaa      960
tcagatacat ccagcaatca tgctgtgctg aagctagcca aaggggatga ggtttggctg     1020
cgaatgggca atggcgctct ccatggggac caccaacgct tctccacctt tgcaggattc     1080
ctgctctttg aaactaagta aatatatgac tagaatagct ccactttggg aagacttgt      1140 agctgagctg atttgttacg atctgaggaa cattaaagtt gagggtttta cattgctgta     1200
ttcaaaaaat tattggttgc aatgttgttc acgctacagg tacaccaata atgttggaca     1260
attcaggggc tcagaagaat caaccacaaa atagtcttct cagatgacct tgactaatat     1320
actcagcatc tttatcactc tttccttggc acctaaaaga taattctcct ctgacgcagg     1380
ttggaaatat ttttttctat cacagaagtc atttgcaaag aatttgact actctgcttt      1440 taatttaata ccagttttca ggaaccctg aagttttaag ttcattattc tttataacat      1500
ttgagagaat cggatgtagt gatatgacag ggctggggca agaacagggg cactagctgc     1560
cttattagct aatttagtgc cctccgtgtt cagcttagcc tttgacccctt tccttttgat    1620 ccacaaaata cattaaaact ctgaattcac atacaatgct attttaaagt caatagattt     1680
tagctataaa gtgcttgacc agtaatgtgg ttgtaatttt gtgtatgttc ccccacatcg     1740
cccccaactt cggatgtggg gtcaggaggt tgaggttcac tattaacaaa tgtcataaat     1800
atctcataga ggtacagtgc caatagatat tcaaatgttg catgttgacc agagggattt     1860
tatatctgaa gaacatacac tattaataaa taccttagag aaagattttg acctggcttt     1920
agataaaact gtggcaagaa aaatgtaatg agcaatatat ggaaataaac acacctttgt     1980
taaagatact ttctaaactt gtgtttaata aactttaata gtcatagaat tgtaaatcac     2040
tatggttaac agaaagtgaa aatattttca tgcagatgat gtgaacagcc atgtgaatag     2100
gtgacttggg cacacagcag ggtcatatga cttcagaaaa cttcgcttt cagttattcc      2160 attgttataa tgtcaacccct ttaagacatt gatgtttaga gggctcacaa ataaaatctg    2220
aatacctgta aggaaagagg ttttttatca cataccttaa gtctttgtaa tgttcatgct     2280
taaattctaa gttttcacct tagtgacaca caaggtttgg ttgtaggcaa caagtcccag     2340
gtgtgtggga aattgattca caacagagat gggaaaggt gcagataatt tccaatgcct      2400
tcacaattta cccatgacca gaaatatact tggaagactg atttcacaag tgtcccaaaa     2460
ctgagatgct aaaaaggaaa cagtaggtag gtgtcatagg aaatttacat gtaccatcta     2520
ataaacaaac ttgcaaattc taaatctttt ttttttttga cagtttca cgctgctgcc       2580 caggctggag tgcagtggca tgatctcagc tcaccgcagc ctccgcctcc tgggttcaag     2640
tgactctcct acctcagcct cctgagtagc tgggactaca ggcgcccacc accaggacca     2700
gctaattttt aatgtttcta atagagatgg ggtttcacca tgttgaccag gccggtctgg     2760
aactcctgac ctcaggtgat ctgcctgcct cggtcttcca aagtgctggg attacaggcg     2820 tgagccccccg cacccagccg caaattctaa atccttaaaac aactctgcaa acgaagcact   2880 tgagttctg cttgcttcag ggatgtaata tggtgtagaa ctgtttcaca taatgatcag      2940
```

```
ccttggtaat tttccagtgt agaaaacatt atatttgacc cttggacaac aaagagatta      3000
tattgaagga attttattga ttgtatcatg aataaaagct gaagtcaaaa ttaaaatgta      3060
aaaaaataat tcagaggatg gaatatgcaa atgtaaactc caaatgatgt ggctggaatt      3120
cataaacatt tactttatgc aagatactgt gctattccag gcactcctat ggcatttaaa      3180
gtacaattct taccttccct aattttcaa cctagtagag gacaataggc taagggaat        3240 aagtacatgg ataacaaaac ataaagtaga atgttttac agccatagaa ggcaaagggc       3300
taggaattca caggagagag aaacagtatc tagctgagag cataagaaaa gcttgtggaa      3360
aagataatat ctgatggcca gagacaattt cttgctttgg tatgtttgaa gtgttatatt     3420
taaatatata tattttattt taaaaaactc actatagaaa atttataaaa ttccccaaaa     3480
tatttagtat aaaattaatc atcccatcaa atattaaata atattactat tttaaagtgt    3540
ttatttcagt cttttcctgc atgtatttat ggcttttatt tttaaatata gtaataaaat    3600
aatttgaaat tagcttttta tatattttg tatcttgctc taatgggttg gactaaacat    3660
attaagaaca ctctcaaatg ctactaagga caatttgaaa acataatttt aatgactgca   3720
taatttattt aactttcctg ttttggaaaa tattattttt tttttattac aaataatatg   3780
tcatgagcat tctctttta aaaaaataaa ctatgtgtgc atataaaaaa aaaaaaaaaa     3840
aaa                                                                   3843
```

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
gcaattattc cccatgaacg                                                  20

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
ggcctcacta aaccatccaa                                                  20

<210> SEQ ID NO 7
<211> LENGTH: 21
<212> TYPE: DNA
<213> ORGANISM: Artificial Sequence
<220> FEATURE:
<223> OTHER INFORMATION: PCR primer

<400> SEQUENCE: 7
agtgtgacgt tgacatccgt a                                                21

<210> SEQ ID NO 8
<211> LENGTH: 22
<212> TYPE: DNA
<213> ORGANISM: Artificial Sequence
<220> FEATURE:
<223> OTHER INFORMATION: PCR primer

<400> SEQUENCE: 8
gccagagcag taatctcctt ct                                               22

-continued

<210> SEQ ID NO 9
<211> LENGTH: 19
<212> TYPE: DNA
<213> ORGANISM: Artificial Sequence
<220> FEATURE:
<223> OTHER INFORMATION: PCR primer

<400> SEQUENCE: 9
acaaggcctc agggtacca                                                    19

<210> SEQ ID NO 10
<211> LENGTH: 20
<212> TYPE: DNA
<213> ORGANISM: Artificial Sequence
<220> FEATURE:
<223> OTHER INFORMATION: PCR primer

<400> SEQUENCE: 10
gccgaaagaa gcccttacag                                                   20

<210> SEQ ID NO 11
<211> LENGTH: 21
<212> TYPE: DNA
<213> ORGANISM: Artificial Sequence
<220> FEATURE:
<223> OTHER INFORMATION: PCR primer

<400> SEQUENCE: 11
gctgcggaaa cttcagaaaa t                                                 21

<210> SEQ ID NO 12
<211> LENGTH: 23
<212> TYPE: DNA
<213> ORGANISM: Artificial Sequence
<220> FEATURE:
<223> OTHER INFORMATION: PCR primer

<400> SEQUENCE: 12
agagacgtgt cactcctgga ctt                                               23

<210> SEQ ID NO 13
<211> LENGTH: 21
<212> TYPE: DNA
<213> ORGANISM: Artificial Sequence
<220> FEATURE:
<223> OTHER INFORMATION: PCR primer

<400> SEQUENCE: 13
caccaacggg ctcatcttct a                                                 21

<210> SEQ ID NO 14
<211> LENGTH: 25
<212> TYPE: DNA
<213> ORGANISM: Artificial Sequence
<220> FEATURE:
<223> OTHER INFORMATION: PCR primer

<400> SEQUENCE: 14
caaaatgacc tagccttcta tcgaa                                             25

<210> SEQ ID NO 15
<211> LENGTH: 20
<212> TYPE: DNA
<213> ORGANISM: Artificial Sequence
<220> FEATURE:

```
<223> OTHER INFORMATION: PCR primer

<400> SEQUENCE: 15
gtgccatcgt ctgcaagatt                                                    20

<210> SEQ ID NO 16
<211> LENGTH: 20
<212> TYPE: DNA
<213> ORGANISM: Artificial Sequence
<220> FEATURE:
<223> OTHER INFORMATION: PCR primer

<400> SEQUENCE: 16
ctggatagga tccaccagga                                                    20

<210> SEQ ID NO 17
<211> LENGTH: 21
<212> TYPE: DNA
<213> ORGANISM: Artificial Sequence
<220> FEATURE:
<223> OTHER INFORMATION: PCR primer

<400> SEQUENCE: 17
gcgctacttc cgagactact t                                                  21

<210> SEQ ID NO 18
<211> LENGTH: 20
<212> TYPE: DNA
<213> ORGANISM: Artificial Sequence
<220> FEATURE:
<223> OTHER INFORMATION: PCR primer

<400> SEQUENCE: 18
gggccttatg ccaggaaact                                                    20

<210> SEQ ID NO 19
<211> LENGTH: 21
<212> TYPE: DNA
<213> ORGANISM: Artificial Sequence
<220> FEATURE:
<223> OTHER INFORMATION: PCR primer

<400> SEQUENCE: 19
catcctcttt tgccacaaca t                                                  21

<210> SEQ ID NO 20
<211> LENGTH: 20
<212> TYPE: DNA
<213> ORGANISM: Artificial Sequence
<220> FEATURE:
<223> OTHER INFORMATION: PCR primer

<400> SEQUENCE: 20
acagaatgtc tttgcgtcca                                                    20

<210> SEQ ID NO 21
<211> LENGTH: 19
<212> TYPE: DNA
<213> ORGANISM: Artificial Sequence
<220> FEATURE:
<223> OTHER INFORMATION: PCR primer

<400> SEQUENCE: 21
ctcctggttg cagaggaga                                                     19
```

```
<210> SEQ ID NO 22
<211> LENGTH: 20
<212> TYPE: DNA
<213> ORGANISM: Artificial Sequence
<220> FEATURE:
<223> OTHER INFORMATION: PCR primer

<400> SEQUENCE: 22
agcagctttg cactcagatg                                               20

<210> SEQ ID NO 23
<211> LENGTH: 20
<212> TYPE: DNA
<213> ORGANISM: Artificial Sequence
<220> FEATURE:
<223> OTHER INFORMATION: PCR primer

<400> SEQUENCE: 23
ggaggatgaa gtgacccaga                                               20

<210> SEQ ID NO 24
<211> LENGTH: 20
<212> TYPE: DNA
<213> ORGANISM: Artificial Sequence
<220> FEATURE:
<223> OTHER INFORMATION: PCR primer

<400> SEQUENCE: 24
ccagtttttg aggctgctgt                                               20

<210> SEQ ID NO 25
<211> LENGTH: 20
<212> TYPE: DNA
<213> ORGANISM: Artificial Sequence
<220> FEATURE:
<223> OTHER INFORMATION: PCR primer

<400> SEQUENCE: 25
tgtctggttt gagcgttctg                                               20

<210> SEQ ID NO 26
<211> LENGTH: 20
<212> TYPE: DNA
<213> ORGANISM: Artificial Sequence
<220> FEATURE:
<223> OTHER INFORMATION: PCR primer

<400> SEQUENCE: 26
ttctgggaag atgaggatgg                                               20

<210> SEQ ID NO 27
<211> LENGTH: 22
<212> TYPE: DNA
<213> ORGANISM: Artificial Sequence
<220> FEATURE:
<223> OTHER INFORMATION: PCR primer

<400> SEQUENCE: 27
taagatggcc ttctacaacg gc                                            22

<210> SEQ ID NO 28
<211> LENGTH: 23
<212> TYPE: DNA
<213> ORGANISM: Artificial Sequence
<220> FEATURE:
<223> OTHER INFORMATION: PCR primer
```

<400> SEQUENCE: 28
ccatacaggt atttgacgtg gag                                          23

<210> SEQ ID NO 29
<211> LENGTH: 20
<212> TYPE: DNA
<213> ORGANISM: Artificial Sequence
<220> FEATURE:
<223> OTHER INFORMATION: PCR primer

<400> SEQUENCE: 29
cagccaggtt ctacgccaag                                              20

<210> SEQ ID NO 30
<211> LENGTH: 22
<212> TYPE: DNA
<213> ORGANISM: Artificial Sequence
<220> FEATURE:
<223> OTHER INFORMATION: PCR primer

<400> SEQUENCE: 30
tgatgctcat gttatccacg gt                                           22

<210> SEQ ID NO 31
<211> LENGTH: 21
<212> TYPE: DNA
<213> ORGANISM: Artificial Sequence
<220> FEATURE:
<223> OTHER INFORMATION: PCR primer

<400> SEQUENCE: 31
ctgcttgcct acctgaagac c                                            21

<210> SEQ ID NO 32
<211> LENGTH: 21
<212> TYPE: DNA
<213> ORGANISM: Artificial Sequence
<220> FEATURE:
<223> OTHER INFORMATION: PCR primer

<400> SEQUENCE: 32
gatacggcgg tataggtgct t                                            21

<210> SEQ ID NO 33
<211> LENGTH: 22
<212> TYPE: DNA
<213> ORGANISM: Artificial Sequence
<220> FEATURE:
<223> OTHER INFORMATION: PCR primer

<400> SEQUENCE: 33
ccagtttcta tgtcacctgg tc                                           22

<210> SEQ ID NO 34
<211> LENGTH: 22
<212> TYPE: DNA
<213> ORGANISM: Artificial Sequence
<220> FEATURE:
<223> OTHER INFORMATION: PCR primer

<400> SEQUENCE: 34
gcagagtctg gcattgatct tg                                           22

<210> SEQ ID NO 35
<211> LENGTH: 21

```
<212> TYPE: DNA
<213> ORGANISM: Artificial Sequence
<220> FEATURE:
<223> OTHER INFORMATION: PCR primer

<400> SEQUENCE: 35
cacacgtact ctatgcgcta c                                               21

<210> SEQ ID NO 36
<211> LENGTH: 21
<212> TYPE: DNA
<213> ORGANISM: Artificial Sequence
<220> FEATURE:
<223> OTHER INFORMATION: PCR primer

<400> SEQUENCE: 36
aagaagagca ccatgttctg g                                               21

<210> SEQ ID NO 37
<211> LENGTH: 21
<212> TYPE: DNA
<213> ORGANISM: Artificial Sequence
<220> FEATURE:
<223> OTHER INFORMATION: PCR primer

<400> SEQUENCE: 37
agcttgattg tcaacctcct g                                               21

<210> SEQ ID NO 38
<211> LENGTH: 19
<212> TYPE: DNA
<213> ORGANISM: Artificial Sequence
<220> FEATURE:
<223> OTHER INFORMATION: PCR primer

<400> SEQUENCE: 38
ccgttggtgt agggcttgt                                                  19

<210> SEQ ID NO 39
<211> LENGTH: 21
<212> TYPE: DNA
<213> ORGANISM: Artificial Sequence
<220> FEATURE:
<223> OTHER INFORMATION: PCR primer

<400> SEQUENCE: 39
cgactcgcta tctccaagtg a                                               21

<210> SEQ ID NO 40
<211> LENGTH: 20
<212> TYPE: DNA
<213> ORGANISM: Artificial Sequence
<220> FEATURE:
<223> OTHER INFORMATION: PCR primer

<400> SEQUENCE: 40
gttgaaccag tctccgacca                                                 20

<210> SEQ ID NO 41
<211> LENGTH: 21
<212> TYPE: DNA
<213> ORGANISM: Artificial Sequence
<220> FEATURE:
<223> OTHER INFORMATION: PCR primer

<400> SEQUENCE: 41
```

```
ctgcataacg gtctggactt c                                        21

<210> SEQ ID NO 42
<211> LENGTH: 19
<212> TYPE: DNA
<213> ORGANISM: Artificial Sequence
<220> FEATURE:
<223> OTHER INFORMATION: PCR primer

<400> SEQUENCE: 42
cagcaactgc ccgtactcc                                           19

<210> SEQ ID NO 43
<211> LENGTH: 19
<212> TYPE: DNA
<213> ORGANISM: Artificial Sequence
<220> FEATURE:
<223> OTHER INFORMATION: PCR primer

<400> SEQUENCE: 43
catctggtgg cacctgctg                                           19

<210> SEQ ID NO 44
<211> LENGTH: 20
<212> TYPE: DNA
<213> ORGANISM: Artificial Sequence
<220> FEATURE:
<223> OTHER INFORMATION: PCR primer

<400> SEQUENCE: 44
tgacacaggc aaaatgggag                                          20

<210> SEQ ID NO 45
<211> LENGTH: 8
<212> TYPE: PRT
<213> ORGANISM: Artificial sequence
<220> FEATURE:
<223> OTHER INFORMATION: FLAG epitope

<400> SEQUENCE: 45

Asp Tyr Lys Asp Asp Asp Asp Lys
1               5
```

METHODS FOR TREATING OR PREVENTING FATTY LIVER DISEASE USING CTRP3

CROSS-REFERENCE TO RELATED APPLICATIONS

This application is a 35 U.S.C. §371 National Stage Entry of International Application No. PCT/US14/24193 having an international filing date of Mar. 12, 2014, which claims the benefit of U.S. Provisional Application No. 61/789,430 filed Mar. 15, 2013, the content of each of the aforementioned applications is herein incorporated by reference in its entirety.

FEDERALLY SPONSORED RESEARCH OR DEVELOPMENT

This invention was made with government support under DK079637 (NIDDK), DK084171, and F32DK084607 (National Research Service Award) awarded by the National Institutes of Health (NIH). The government has certain rights in the invention.

INCORPORATION-BY-REFERENCE OF MATERIAL SUBMITTED ELECTRONICALLY

This application contains a sequence listing. It has been submitted electronically via EFS-Web as an ASCII text file entitled "111232-00444$_{13}$ST25.txt". The sequence listing is 24,576 bytes in size, and was created on Nov. 8, 2016. It is hereby incorporated by reference in its entirety.

BACKGROUND

Hepatic steatosis, or fatty liver, results from an imbalance between production and removal of hepatic triglycerides (TAGs) (Cohen et al., 2011). This imbalance can result from excessive alcohol consumption (alcoholic fatty liver disease) or through other means (non-alcoholic fatty liver disease, NAFLD). In NAFLD, elevated hepatic TAG (triacylglycerol) is caused by a combination of excess dietary lipids and de novo fatty acid synthesis (Cohen et al., 2011; Browning and Horton, 2004; Postic and Girard, 2008). Fat oxidation and TAG export (in the form of very low-density lipoprotein, VLDL) aid in removal of hepatic TAGs. NAFLD is one of the primary causes of abnormal liver function (Cohen et al., 2011), frequently linked to hepatic insulin resistance and uncontrolled gluconeogenesis in the diabetic state (Browning and Horton, 2004; Kotronen et al., 2008; Kotronen et al., 2007; Sunny et al., 2011; Jornayvaz et al., 2011; Kim et al., 2001). Indeed, up to 70% of clinically obese patients have NAFLD (Luyckx et al., 1998). Further, obese patients with NAFLD are at a significantly higher risk of developing obesity-associated co-morbidities (e.g., heart disease and type 2 diabetes) (Treeprasertsuk et al., 2012). For reasons still poorly understood, a subset of patients with NAFLD will go on to develop NASH (nonalchoholic steatohepatitis) and cirrhosis (Cohen et al., 2011). Despite the prevalence of NAFLD in the general population (Lazo and Clark, 2008; Szczepaniak et al., 2005), therapeutic options are limited.

CTRP3 (C1q/TNF-related protein) is a secreted plasma protein of the C1q family that helps regulate hepatic gluconeogenesis and is down-regulated in a diet-induced obese state. However, the role of CTRP3 in regulating lipid metabolism has not been established.

SUMMARY

In one aspect, the presently disclosed subject matter provides methods for treating or preventing fatty liver disease.

In some aspects, the presently disclosed subject matter provides a method for treating or preventing fatty liver disease in a subject in need thereof, the method comprising administering to the subject a therapeutically effective amount of a C1q/TNF-related protein 3 (CTRP3) polypeptide or a functional variant thereof, wherein the CTRP3 polypeptide or functional variant thereof comprises an amino acid sequence at least 90% identical to the amino acid sequence of SEQ ID NO:1 or SEQ ID NO:3. In other aspects, the CTRP3 polypeptide or functional variant thereof is a functional fragment of an amino acid sequence at least 90% identical to the amino acid sequence of SEQ ID NO:1 or SEQ ID NO:3. In still other aspects, the CTRP3 polypeptide or functional variant thereof is fused to a heterologous polypeptide, particularly an epitope tag at a carboxyl-terminus of the CTRP3 polypeptide such as a Flag-polypeptide tag. In other aspects, the fatty liver disease is selected from the group consisting of non-alcoholic fatty liver disease (NAFLD), alcoholic fatty liver disease (AFLD), non-alcoholic steatohepatitis (NASH), alcoholic steatohepatitis (ASH), NASH-associated liver fibrosis, ASH-associated liver fibrosis, non-alcoholic cirrhosis, and alcoholic cirrhosis.

In further aspects, the methods of the presently disclosed subject matter comprise a method for treating or preventing fatty liver disease in a subject in need thereof, the method comprising administering to the subject a therapeutically effective amount of a nucleic acid molecule encoding a CTRP3 polypeptide or a functional variant thereof, wherein the nucleic acid molecule comprises a nucleotide sequence selected from the group consisting of: a) a nucleotide sequence at least 90% identical to the nucleotide sequence of SEQ ID NO: 2 or SEQ ID NO:4; and b) a nucleotide sequence that encodes the amino acid sequence of SEQ ID NO:1 or SEQ ID NO:3. In other aspects, the nucleic acid molecule encoding the CTRP3 polypeptide or functional variant thereof is introduced into the subject in a manner permitting expression of the CTRP3 polypeptide or functional variant thereof, particularly wherein the nucleic acid molecule encoding the CTRP3 polypeptide or functional variant thereof is introduced into the subject by a viral vector or a transformed host cell. In other aspects, the nucleic acid molecule encodes a CTRP3 polypeptide or a functional variant thereof that is a functional fragment of an amino acid sequence at least 90% identical to the amino acid sequence of SEQ ID NO:1 or SEQ ID NO:3. In still other aspects, the nucleic acid molecule encodes a CTRP3 polypeptide or functional variant thereof fused to a heterologous polypeptide, particularly an epitope tag at a carboxyl-terminus of the CTRP3 polypeptide such as a Flag-polypeptide tag. In other aspects, the fatty liver disease is selected from the group consisting of non-alcoholic fatty liver disease (NAFLD), alcoholic fatty liver disease (AFLD), non-alcoholic steatohepatitis (NASH), alcoholic steatohepatitis (ASH), NASH-associated liver fibrosis, ASH-associated liver fibrosis, non-alcoholic cirrhosis, and alcoholic cirrhosis.

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

Having thus described the presently disclosed subject matter in general terms, reference will now be made to the accompanying Drawings, which are not necessarily drawn to scale, and wherein:

FIGS. 1A-1B show the amino acid (A; SEQ ID NO: 1) and nucleotide (B; SEQ ID NO: 2) sequences for human CTRP3, variant 1. CTRP3, variant 1 represents a shorter transcript and encodes the shorter isoform A of CTRP3.

Figure 3:
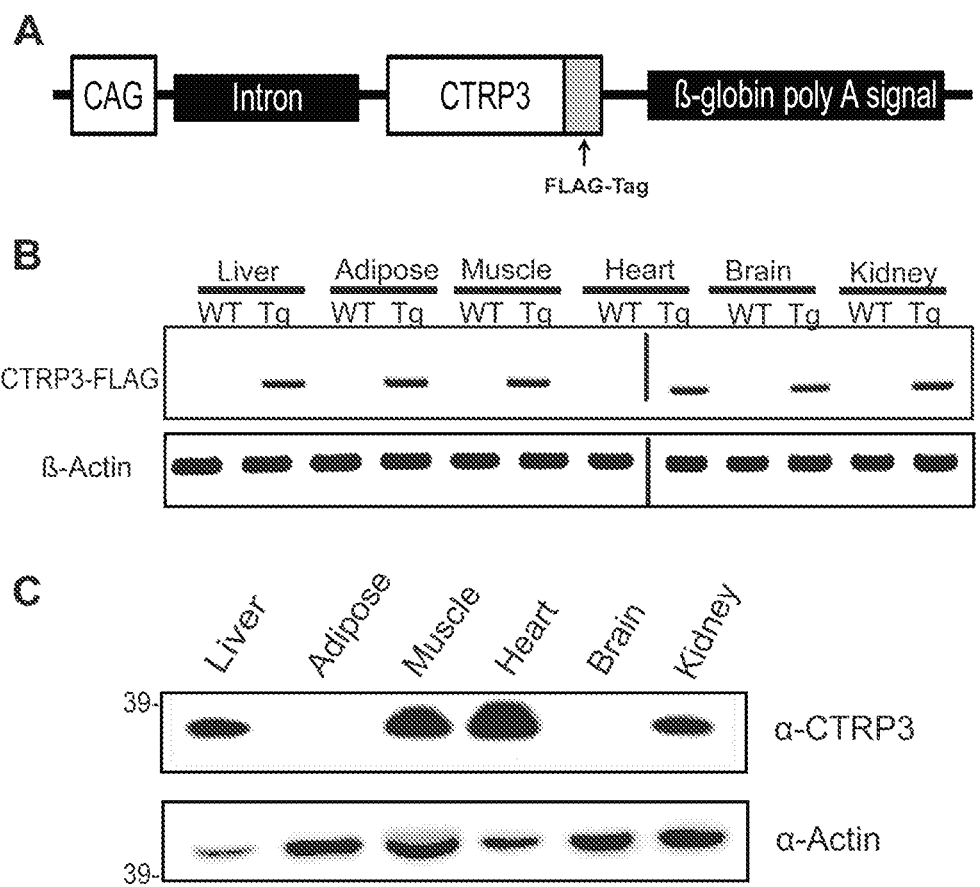
Figure 6:
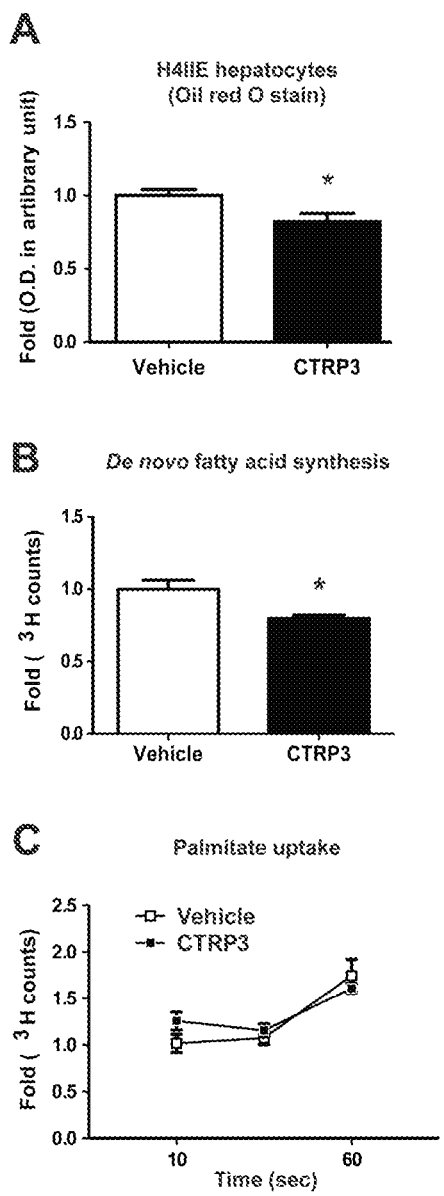

FIGS. 2A-2B show the amino acid (A; SEQ ID NO: 3) and nucleotide (B; SEQ ID NO: 4) sequences for human CTRP3, variant 2. CTRP3, variant 2 uses an alternate in-frame splice site that results in an additional segment in the 5' coding region compared to variant 1, and represents a longer isoform B of CTRP3;

FIGS. 3A-3C show the generation of CTRP3 Tg mice. (A) Schematic of CTRP3 transgenic construct. FLAG-tagged CTRP3 transgene is driven by a ubiquitous CAG promoter. (B) Semi-quantitative RT-PCR analysis of CTRP3 transgene expression in mouse tissues. β-actin was included as control. (C) Immunoblot analysis for the presence of CTRP3-FLAG protein in mouse tissues. β-actin levels serve as loading control. WT, wild-type; Tg, Transgenic;

FIGS. 4A-4H show improved insulin tolerance in Tg mice without changes in other metabolic parameters. (A) No differences in body weight gain over time between WT and Tg male mice fed an HFD (high-fat diet). (B) Food intake in Tg and WT mice. (C) Total body mass, fat mass, and lean mass of HFD-fed WT and Tg mice. (D-F) Indirect calorimetry analysis of oxygen consumption ($VO_2$; D), energy expenditure (E), respiratory exchange ratio (RER=$VCO_2$/$VO_2$; F) in HFD-fed Tg and WT mice. (G) Glucose tolerance test on HFD-fed Tg and WT mice. (H) Insulin tolerance test on HFD-fed Tg and WT mice. Body weight measurements and glucose and insulin tolerance tests were repeated with multiple cohorts of HFD-fed WT and Tg mice (n=8-10 per group). Data reported are the results from one cohort, with results similar across cohorts. Data are reported as mean+SEM of 8-10 mice per group. *$p<0.05$ vs. WT. LFD, Low-fat diet; HFD, High-fat diet. $VO_2$, volume of oxygen consumption; $VCO_2$, volume of carbon dioxide produced; RER, respiratory exchange ratio;

FIGS. 5A-5G show reduced hepatic triglyceride content and synthesis in CTRP3 Tg mice. (A) Representative Tg and WT mouse liver sections stained with oil Red O. (B) Quantification of hepatic triglyceride content. (C) Quantification of mRNA expression of gluconeogenic genes in liver, normalized against 18 S rRNA. (D) Quantification of mRNA expression of representative fatty acid oxidation genes in liver, normalized against 18 S rRNA. (E-F) Quantitative immunoblot analysis of liver AMPKα (Thr-172) (E) and Akt (Ser-473) (F) phosphorylation in WT and Tg mice. (G) Quantification of mRNA expression of enzymes involves in triglyceride synthesis. All data are reported as comparisons between WT and Tg mice on an HFD (n=8-10 per group). Phosphorylated protein levels were normalized to total protein levels. All data are reported as mean+SEM. *$p<0.05$ vs. WT;

FIGS. 6A-6C show that recombinant CTRP3 treatment reduces lipid accumulation in vitro. (A) CTRP3 treatment reduces the accumulation of neutral lipids in rat H4IIE hepatocytes treated with palmitate and CTRP3 (5 μg/mL), as quantified by oil red O staining. (B) CTRP3 decreases de novo lipid synthesis in H4IIE hepatocytes, as quantified by 3H-acetate incorporation. (C) No change in lipid uptake as measured by 3H-palmitate uptake by H4IIE hepatocytes pre-treated with vehicle or CTRP3. Values are mean fold+SEM. *$p<0.05$ vs. vehicle;

FIGS. 7A-7B show the reduced export of VLDL-triglycerides from the liver of Tg mice. (A) Triglyceride content was measured in plasma samples taken at 0, 1, 2, 6, and 24 h after poloxamer 407 (lipoprotein lipase inhibitor) administration. (B) Rate of triglyceride accumulation was calculated for each time frame indicated. *$p<0.05$ vs. vehicle. (n=8 mice per group); and FIGS. 8A-8G show that short-term administration of recombinant CTRP3 reduces hepatic triglyceride levels in diet-induced obese (DIO) mice. (A) Time line depicting the daily injection study. After 12 weeks on a high-fat diet, wild-type DIO mice were fasted for 8 h before initial blood draw. After 72-h recovery from the initial fast (considered day 0), body weight of DIO mice was determined CTRP3 (2 μg/g body weight) or vehicle injection was given every 24 h for the next 5 days. After the 5th injection, food was immediately removed and animals were euthanized and liver tissues and sera were harvested after an 8 h fast. (B) Daily body weight of vehicle- and CTRP3-injected DIO mice. (C) Pre- and post-treatment fasting (8 h) blood glucose levels. (D) Hepatic triglyceride contents in vehicle- and CTRP3-injected DIO mice. (E-F) Serum triglyceride (E) and ketones (F) levels in vehicle- and CTRP3-injected DIO mice.

Figure 9:
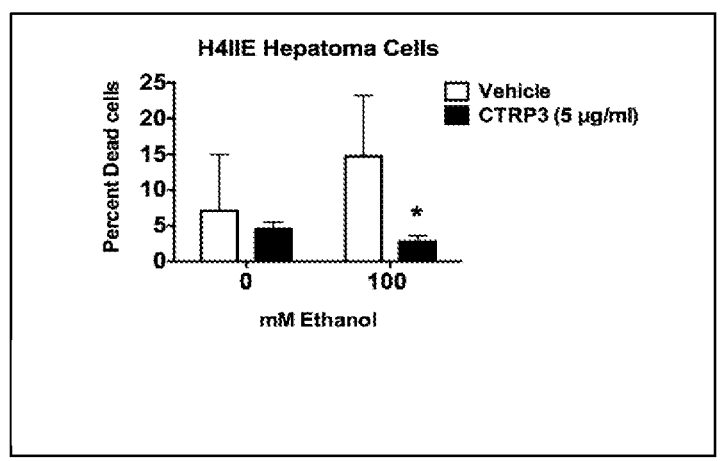
Figure 10:
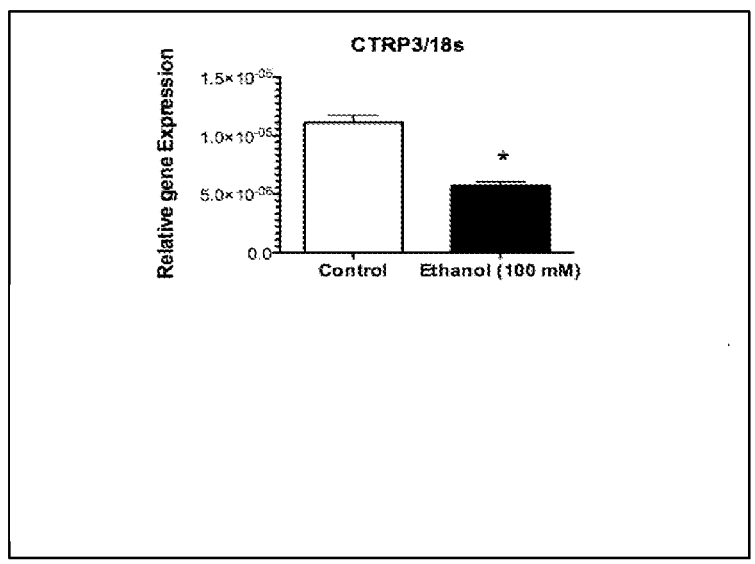

FIG. 9 shows treatment of rat H4IIE hepatocytes overnight (18 hrs) with ethanol (100 mM) and recombinant CTRP3 protein (5 ug/ml). Treatment with CTRP3 significantly reduced the percentage of dead cells (as determined by counting trypan blue positive cells; and FIG. 10 shows the effect of ethanol exposure on the gene expression of CTRP3 from a mouse adipocyte cell line (3T3-L1 adipocyte). CTRP3 levels were suppressed by ethanol.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

As part of an effort to discover novel secreted metabolic regulators, a family of fifteen secreted proteins of the C1q family was recently identified, designated as C1q/TNF-related proteins (CTRP1-15) (Wong et al., 2004; Wong et al., 2009; Wong et al., 2008; Wei et al., 2012; Wei et al., 2011; Seldin et al., 2012). Several of these proteins play important and distinct roles in regulating insulin sensitivity and energy balance (Wong et al., 2009; Wong et al., 2008; Wei et al., 2012; Wei et al., 2011; Peterson et al., 2010; Peterson et al., 2012; Enomoto et al., 2011; Wei et al, 2012). It was recently demonstrated that CTRP3 acts on liver to suppress hepatic glucose output by modulating the expression of gluconeogenic enzymes (Peterson et al., 2010). A cardioprotective function of CTRP3 was recently demonstrated in an animal model of myocardiac infarction (Yi et al., 2012). In addition, several other functions attributable to CTRP3, derived from in vitro studies, have been reported (Akiyama et al., 2006; Akiyama et al., 2007; Akiyama et al., 2009; Maeda et al., 2006; Maeda et al., 2010; Kopp et al., Endocrinology, 2010; Kopp et al., Cytokine, 2010; Wolfing et al., 2008; Hofmann et al., 2011).

The presently disclosed subject matter relates in part to an investigation of the role of CTRP3 in regulating lipid metabolism and its protective function in a pathophysiological context of high-fat feeding. Using a transgenic (Tg) mouse model, along with short-term recombinant protein supplementation, an important and novel role for CTRP3 in regulating hepatic TAG metabolism and its protective function in attenuating fatty liver disease, in particular diet-induced hepatic steatosis, were identified.

I. Methods of Treating or Preventing Fatty Liver Disease using a CTRP3 Polypeptide or a Functional Variant Thereof A. Proteins and Polypeptides In one embodiment, the presently disclosed subject matter provides a method for treating or preventing fatty liver disease in a subject in need thereof, the method comprising administering to the subject a therapeutically effective amount of a CTRP3 polypeptide or a functional variant thereof.

As used herein, the terms "C1q/TNF-related protein 3" or "CTRP3" or "CTRP3 polypeptide" refer to a naturally occurring or endogenous CTRP3 and to proteins having an amino acid sequence which is the same as that of a naturally occurring or endogenous CTRP3 (e.g., recombinant proteins). Accordingly, as defined herein, the term includes mature CTRP3, glycosylated or unglycosylated CTRP3 proteins, polymorphic or allelic variants, and other isoforms of CTRP3 (e.g., produced by alternative splicing or other cellular processes). At least two isoforms of human CTRP3 have been identified. CTRP3, variant 1 represents a shorter transcript and encodes the shorter isoform A of CTRP3 (FIG. 1A shows the amino acid sequence for isoform A of CTRP3 (SEQ ID NO:1); FIG. 1B shows the nucleotide sequence encoding isoform A (SEQ ID NO:2)). CTRP3, variant 2 uses an alternate in-frame splice site that results in an additional segment in the 5' coding region compared to variant 1, and represents a longer isoform B of CTRP3 (FIG. 2A shows the amino acid sequence for isoform B of CTRP3 (SEQ ID NO:3); FIG. 2B shows the nucleotide sequence encoding isoform A (SEQ ID NO:4)). Accordingly, in particular embodiments, CTRP3 refers to a polypeptide having the amino acid sequence of SEQ ID NO:1 or SEQ ID NO:3 or encoded by a nucleic acid molecule having the nucleotide sequence of SEQ ID NO:2 or SEQ ID NO:4.

"Functional variants" of CTRP3 include functional fragments, functional mutant proteins, and/or functional fusion proteins. A functional variant of CTRP3 refers to an isolated and/or recombinant protein or polypeptide which has at least one property, activity and/or function characteristic of CTRP3, such as attenuating hepatic steatosis, reducing hepatic triglyceride content, and/or reducing or inhibiting expression of triglyceride synthesis genes. Generally, fragments or portions of CTRP3 encompassed by the presently disclosed subject matter include those having a deletion (i.e. one or more deletions) of an amino acid (i.e., one or more amino acids) relative to the mature CTRP3 (such as N-terminal, C-terminal or internal deletions). Fragments or portions in which only contiguous amino acids have been deleted or in which non-contiguous amino acids have been deleted relative to mature CTRP3 are also envisioned. Generally, mutants or derivatives of CTRP3, encompassed by the present invention include natural or artificial variants differing by the addition, deletion and/or substitution of one or more contiguous or non-contiguous amino acid residues, or modified polypeptides in which one or more residues is modified, and mutants comprising one or more modified residues. Preferred mutants are natural or artificial variants of CTRP3 differing by the addition, deletion and/or substitution of one or more contiguous or non-contiguous amino acid residues.

Generally, the CTRP3 or functional variant thereof has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:1 or SEQ ID NO:3 over the length of the variant.

In some embodiments, the amino acid sequences of SEQ ID NO:1 or SEQ ID NO:3 are used to make purified protein of CTRP3, for example, using currently available recombinant protein production. Amino acid sequence identity can be determined using a suitable amino acid sequence alignment algorithm, such as CLUSTAL W, using the default parameters (Thompson J. D. et al., 1994). CTRP3 proteins and functional variants thereof can be produced using well-known methods, such as recombinant expression and purification, chemical synthesis (e.g., synthetic peptides), or by combinations of biological and chemical methods, and recombinant proteins or polypeptides which are isolated. The proteins can be obtained in an isolated state of at least about 50% by weight, preferably at least about 75% by weight, and more preferably, in essentially pure form. Proteins or polypeptides referred to herein as "recombinant" are proteins or polypeptides produced by the expression of recombinant nucleic acids.

Accordingly, in one embodiment the presently disclosed subject matter provides a method for treating or preventing fatty liver disease in a subject in need thereof, the method comprising administering to the subject a therapeutically effective amount of a CTRP3 polypeptide or a functional variant thereof, wherein the CTRP3 polypeptide or functional variant thereof comprises an amino acid sequence at least 90% identical to the amino acid sequence of SEQ ID NO:1 or SEQ ID NO:3. In one embodiment, the CTRP3 polypeptide or functional variant thereof is a functional fragment of an amino acid sequence at least 90% identical to the amino acid sequence of SEQ ID NO:1 or SEQ ID NO:3.

In other embodiments, the presently disclosed subject matter provides chimeric molecules comprising any of the herein described CTRP3 polypeptides or functional variants thereof fused to a heterologous polypeptide or amino acid sequence. Examples of such chimeric molecules comprise any of the herein described polypeptides fused to an epitope tag sequence or a Fc region of an immunoglobulin.

The term "epitope tagged" when used herein refers to a chimeric polypeptide comprising a CTRP3 polypeptide or functional variant thereof fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

In one embodiment, the presently disclosed subject matter provides a chimeric molecule comprising a fusion of a CTRP3 polypeptide or functional variant thereof with a tag polypeptide which provides an epitope to which an anti-tag antibody can selectively bind. The epitope tag is generally placed at the amino- or carboxyl-terminus of the CTRP3 polypeptide or functional variant thereof The presence of such epitope-tagged forms of the CTRP3 polypeptides or functional variants thereof can be detected using an antibody against the tag polypeptide. Also, provision of the epitope tag enables the CTRP3 polypeptides or functional variants thereof to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., 1988)); the c-myc tag and the 8F9, 3C7, 6E10, G4, B7 and 9E10 antibodies thereto (Evan et al., 1985); and the Herpes Simplex virus glycoprotein D (gD) tag and its antibody (Paborsky et al., (1990)). Other tag polypeptides include the Flag-peptide (Hopp et al., (1988)); the KT3 epitope peptide (Martin et al., (1992)); an α-tubulin epitope peptide (Skinner et al., (1991)); and the T7 gene 10 protein peptide tag (Lutz-Freyermuth et al., (1990)).

Accordingly, in one embodiment, the presently disclosed subject matter provides a method for treating or preventing fatty liver disease in a subject in need thereof, the method comprising administering to the subject a therapeutically effective amount of a CTRP3 polypeptide or a functional variant thereof, wherein the CTRP3 polypeptide or functional variant thereof is fused to a heterologous polypeptide. In a particular embodiment, the heterologous polypeptide is an epitope tag. In a further particular embodiment the epitope tag is placed at a carboxyl-terminus of the CTRP3 polypeptide. In yet another particular embodiment, the epitope tag is a Flag-polypeptide tag.

B. Nucleic Acid Molecules and Gene Expression Systems

In another embodiment, the presently disclosed subject matter provides a method for treating or preventing fatty liver disease in a subject in need thereof, the method comprising administering to the subject a therapeutically effective amount of a nucleic acid molecule encoding a CTRP3 polypeptide or a functional variant thereof.

Isolated and/or recombinant (including, e.g., essentially pure) nucleic acid molecules comprising nucleotide sequences which encode CTRP3 or functional variants thereof can be administered to cause CTRP3 production in situ or in vivo. Nucleic acid molecules referred to herein as "isolated" are nucleic acid molecules separated away from the nucleic acid molecules of the genomic DNA or cellular RNA of their source of origin (e.g., as it exists in cells or in a mixture of nucleic acid molecules such as a library), and may have undergone further processing. "Isolated" nucleic acid molecules include nucleic acid molecules obtained by methods described herein, similar methods or other suitable methods, including essentially pure nucleic acid molecules, nucleic acid molecules produced by chemical synthesis, by combinations of biological and chemical methods, and recombinant nucleic acid molecules which are isolated. Nucleic acid molecules referred to herein as "recombinant" are nucleic acid molecules which have been produced by recombinant DNA methodology, including those nucleic acid molecules that are generated by procedures which rely upon a method of artificial recombination, such as the polymerase chain reaction (PCR) and/or cloning into a vector using restriction enzymes. "Recombinant" nucleic acid molecules are also those that result from recombination events that occur through the natural mechanisms of cells, but are selected for after the introduction to the cells of nucleic acid molecules designed to allow and make probable a desired recombination event.

Isolated and/or recombinant nucleic acid molecules meeting these criteria comprise nucleic acid molecules having nucleotide sequences encoding naturally occurring CTRP3 polypeptides and portions thereof, or functional variants of the naturally occurring sequences. Such variants include mutants differing by the addition, deletion or substitution of one or more residues, modified nucleic acid molecules in which one or more residues is modified (e.g., DNA or RNA analogs), and mutants comprising one or more modified residues. The sequence can be codon-optomized or codon de-optimized for expression in the individual. The nucleic acid molecule can be in the form of DNA or RNA, and can be either single or double stranded. Generally, the nucleic acid molecule is operably linked to expression control sequences such as an origin of replication, a promoter, and an enhancer (see, e.g., Queen, et al., 1986).

In one aspect, the nucleic acid molecule comprising a nucleotide sequence encoding a CTRP3 polypeptide or a functional variant thereof has a nucleotide sequence that is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:2 or SEQ ID NO:4 over the length of the variant. Nucleic acid sequence identity can be determined using a suitable nucleic acid sequence alignment algorithm, such as CLUSTAL W, using the default parameters (Thompson J. D. et al., 1994).

In another aspect the nucleic acid molecule comprising a nucleotide sequence encoding a CTRP3 polypeptide or a functional variant thereof has a nucleotide sequence that encodes the amino acid sequence of SEQ ID NO:1 or SEQ ID NO:3.

Accordingly, in one embodiment, the presently disclosed subject matter provides a method for treating or preventing fatty liver disease in a subject in need thereof, the method comprising administering to the subject a therapeutically effective amount of a nucleic acid molecule encoding a CTRP3 polypeptide or a functional variant thereof, wherein the nucleic acid molecule comprises a nucleotide sequence selected from the group consisting of: a) a nucleotide sequence at least 90% identical to the nucleotide sequence of SEQ ID NO: 2 or SEQ ID NO:4; and b) a nucleotide sequence that encodes the amino acid sequence of SEQ ID NO:1 or SEQ ID NO:3. In one embodiment, the nucleic acid molecule encodes a CTRP3 polypeptide or functional variant thereof that is a functional fragment of an amino acid sequence at least 90% identical to the amino acid sequence of SEQ ID NO:1 or SEQ ID NO:3. In another embodiment, the nucleic acid molecule comprises a nucleotide sequence that encodes a CTRP3 polypeptide or functional variant thereof fused to a heterologous polypeptide. In a particular embodiment, the heterologous polypeptide is an epitope tag. In a further particular embodiment the epitope tag is placed at a carboxyl-terminus of the CTRP3 polypeptide. In yet another particular embodiment, the epitope tag is a Flag-polypeptide tag.

A number of suitable vectors for expression of recombinant proteins in desired cells are well-known and conventional in the art. Suitable vectors can contain a number of components, including, but not limited to one or more of the following: an origin of replication; a selectable marker gene; one or more expression control elements, such as a transcriptional control element (e.g., a promoter, an enhancer, a terminator), and/or one or more translation signals; and a signal sequence or leader sequence for targeting to the secretory pathway in a selected host cell. If desired, the vector can include a detectable marker.

Accordingly, in some embodiments, the presently disclosed subject matter provides vectors comprising nucleotide sequences encoding any of the herein described CTRP3 polypeptides or functional variants thereof. Host cells comprising any such vector and/or transformed to express a CTRP3 polypeptide or functional variant thereof are also provided. A process for producing any of the herein described polypeptides is further provided and comprises culturing host cells under conditions suitable for expression of the desired polypeptide and recovering the desired polypeptide from the host cell or administering a transformed host cell to a subject.

In certain embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are known.

Methods by which expression vectors may be introduced into cells are known in the art. In certain embodiments of the presently disclosed subject matter, the expression construct comprises a virus or engineered construct derived from a viral genome. The ability of certain viruses to enter cells via receptor-mediated endocytosis, to integrate into host cell genome, and express viral genes stably and efficiently have made them attractive candidates for the transfer of foreign genes into mammalian cells (Nicolas and Rubinstein, 1988; Baichwal and Sugden, 1986; Temin, 1986). Preferred gene therapy vectors are generally viral vectors.

Accordingly, in another embodiment, the presently disclosed subject matter provides a method for treating or preventing fatty liver disease in a subject in need thereof, the method comprising administering to the subject a therapeutically effective amount of a nucleic acid molecule encoding a CTRP3 polypeptide or a functional variant thereof, wherein the nucleic acid molecule encoding the CTRP3 polypeptide or functional variant thereof is introduced into the subject in a manner permitting expression of the CTRP3 polypeptide or functional variant thereof. In one embodiment, the nucleic acid molecule encoding the CTRP3 polypeptide or functional variant thereof is introduced into the subject by a viral vector or a transformed host cell.

In other embodiments, the method of introducing the nucleic acid molecule encoding the CTRP3 polypeptide or functional variant thereof into the subject in a manner permitting expression of the CTRP3 polypeptide or functional variant thereof comprises methods selected from the group consisting of electroporation, DEAE Dextran transfection, calcium phosphate transfection, cationic liposome fusion, proptoplast fusion, creation of an in vivo electric field, DNA-coated microprojectile bombardment, injection with recombinant replication-defective viruses, homologous recombination, in vivo gene therapy, ex vivo gene therapy, viral vectors, and naked DNA transfer.

C. Methods of Treating or Preventing Fatty Liver Disease

As used herein, the terms "hepatic steatosis" and "fatty liver" are interchangeable, and refer to fatty infiltration of the liver characterized by an excessive deposition of fat in the liver and its cells. This condition is generally associated with patients suffering from such conditions as chronic alcoholism, alcoholic cirrhosis, exogenous obesity, metabolic disorders such as diabetes mellitus, and other like diseases where fatty liver is a histologic abnormality. In these cases, the patient usually presents an enlarged palpable tender liver; elevated liver function test values; and a large amount of fat infiltration on examination of a biopsy of the liver.

Fatty liver disease encompasses a spectrum of liver conditions and is typically classified as either alcoholic or nonalcoholic. In either case, fatty liver disease ranges from simple hepatic steatosis (lipid accumulation and deposition) to alcoholic steatohepatitis (NASH) or alcoholic steatohepatitis (ASH), which often progress to hepatic fibrosis, cirrhosis, and potentially hepatocellular carcinoma. Alcoholic (AFLD) and nonalcoholic fatty liver disease (NAFLD) are histologically indistinguishable; however, by definition NAFLD develops in patients who consume little or no alcohol. Instead, NAFLD is frequently found in individuals with obesity, metabolic syndrome, and type 2 diabetes and is closely linked to insulin resistance (Utzschneider et al., 2006). With the dramatic recent increase in the prevalence of obesity and insulin resistance, NAFLD has surpassed AFLD and viral hepatitis-induced liver disease as the most common chronic liver disease. It has been estimated that approximately 75% of those with obesity have NAFLD and as many as 20% may have NASH (Clark, 2006; Lazo et al., 2008).

In one embodiment, the methods of the presently disclosed subject matter can be used to treat a fatty liver disease selected from the group consisting of non-alcoholic fatty liver disease (NAFLD), alcoholic fatty liver disease (AFLD), non-alcoholic steatohepatitis (NASH), alcoholic steatohepatitis (ASH), NASH-associated liver fibrosis, ASH-associated liver fibrosis, non-alcoholic cirrhosis, and alcoholic cirrhosis.

As used herein "treating" includes achieving, partially or substantially, one or more of the following results: partially or totally reducing the extent of the disease (e.g., reducing fat deposits, increasing insulin activity, reducing weight); ameliorating or improving a clinical symptom or indicator associated with the disorder; delaying, inhibiting or preventing the progression of the disease; or partially or totally delaying, inhibiting or preventing the onset or development of the disease. Delaying, inhibiting or preventing the progression of the disease includes for example, delaying, inhibiting or preventing the progression of normal healthy liver to simple fatty liver (either NAFL or AFL), the progression of NAFL or AFL to NASH or ASH, respectively;

the progression of NASH or ASH to NASH-associated fibrosis or ASH-associated fibrosis, respectively, or the progression of NASH-associated fibrosis or ASH-associated fibrosis to non-alcoholic cirrhosis or alcoholic cirrhosis, respectively. "Treatment" also includes prophylactic treatment of subjects at risk for a fatty liver disease selected from NAFLD, AFLD, NASH, ASH, NASH-associated liver fibrosis, ASH-associated liver fibrosis, and non-alcoholic or alcoholic cirrhosis. "Prophylactic treatment" refers to treatment before onset of a disease to prevent, inhibit or reduce its occurrence.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

"Effective amount": In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

II. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compositions of the disclosure by other methods.

The following Example shows the use of a transgenic mouse model to address the potential function of CTRP3 in ameliorating high-fat diet-induced metabolic stress. Both transgenic and wild-type mice fed a high-fat diet showed similar body weight gain, food intake, and energy expenditure. Despite similar adiposity to wild-type mice upon diet-induced obesity (DIO), CTRP3 transgenic mice were strikingly resistant to the development of hepatic steatosis and demonstrated modest improvement in systemic insulin sensitivity. Serum levels of TNF-α were also reduced in transgenic mice. Additionally, reduced hepatic triglyceride levels were due to decreased expression of enzymes (GPAT, AGPAT, and DGAT) involved in triglyceride synthesis. Importantly, short-term daily administration of recombinant CTRP3 to DIO mice for 5 days was sufficient to improve the fatty liver phenotype, evident as reduced hepatic triglyceride content and expression of triglyceride synthesis genes. Consistent with a direct effect on liver cells, recombinant CTRP3 treatment reduced fatty acid synthesis and neutral lipid accumulation in cultured rat H4IIE hepatocytes. Together, these results establish a novel role for CTRP3 hormone in regulating hepatic lipid metabolism and highlight its protective function and therapeutic potential in attenuating hepatic steatosis.

Example 1

Materials and Methods

Animals—All animal protocols were approved by the Institutional Animal Care and Use Committee of The Johns Hopkins University School of Medicine. CTRP3 Tg mice (on a C57BL/6 genetic background) and control littermates were housed in polycarbonate cages on a 12-h light-dark photocycle with ad libitum access to water and food. Littermates were used throughout the study as wild-type (WT) controls. Mice were fed a high-fat diet (HFD; 60% kcal derived from fat, Research diets; D12492) or the isocaloric-matched low-fat diet (LFD; 10% kcal derived from fat, Research diets; D12450B). Diet was provided for a period of 14 weeks, beginning at 4 weeks of age. Metabolic parameters and food intake were measured using the Comprehensive Laboratory Animal Monitoring System (CLAMS) (Columbus Instruments), and body composition was determined using a whole-body NMR instrument (EchoMRI) as previously described (Peterson et al., 2012). At termination of the study, animals were fasted overnight and euthanized, when tissues were collected, snap frozen in liquid nitrogen, and kept at −80° C. until analysis.

Antibodies and chemicals—Mouse monoclonal anti-FLAG M2 antibody was obtained from Sigma. Antibodies that recognize phospho-AKT (Thr-308), phospho-AMPKα (Thr-172), Akt, and AMPKα were obtained from Cell Signaling Technology. Antibody that recognizes actin (sc1616) was obtained from Santa Cruz Biotechnology, Inc. Polyclonal rabbit antibody recognizing CTRP3 was obtained from Novus Biologicals (NBP 1-02995).

Generation of CTRP3 transgenic mouse line—Carboxy-terminal FLAG epitope (DYKDDDDK) (SEQ. ID NO. 45)-tagged CTRP3 was cloned into the EcoRI site of pCA-GGS vector (Niwa et al., 1991). Expression of Ctrp3 transgene was driven by the ubiquitous CAG promoter, containing a CMV enhancer element with a chicken β-actin promoter. Plasmid construct was digested with SalI and NotI restriction enzymes, and resulting DNA fragments (~3.5 and 2.5 kb) were separated on 1% agarose gel. The ~5-kb linear DNA fragment containing the CAG promoter and enhancer, Ctrp3 transgene, and rabbit β-globin polyA adenylation signal was excised from the agarose gel, purified, and verified by DNA sequencing. Pronuclear injections were performed, and several founder lines (on a C57BL/6 genetic background) expressing the Ctrp3 transgene were obtained. One of these mouse lines was maintained and expanded for phenotypic analysis. Tg mice are fertile with no gross abnormality observed.

Mouse serum analysis—Mouse serum samples were collected at times indicated using microvette® CB 300 (Sarstedt). Glucose concentrations were determined at time of blood collection with a glucometer (BD Biosciences). Serum/tissue TAGs (ThermoFisher Scientific, Waltham, Mass.), non-esterified-fatty acids (NEFA; Wako Diagnostics, Richmond, Va.), insulin, tumor necrosis factor-alpha (TNF-α, and adiponectin (Millipore, Billerica, Mass.) were determined using commercially available kits. For Western blot analysis, serum samples were diluted 1:20 in SDS loading buffer [50 mM Tris-HC1, ph 7.4, 2% SDS w/v, 6% glycerol w/v, 1% 2-mercaptoethanol v/v, and 0.01% bromophenol blue w/v].

Intraperitoneal glucose and insulin tolerance tests—Cohorts of 8-10 Tg and WT control littermates were injected with glucose (1 g/kg) or insulin (0.8 units/kg for LFD-fed mice, 1.2 units/kg for HFD-fed mice). Animals were fasted overnight (16 h) prior to the glucose tolerance test. For the insulin tolerance test, food was removed 2 h prior to insulin injection. Serum samples were collected at the indicated time points. Insulin and glucose tolerance tests were performed when mice were 16 and 17 weeks of age, respectively.

Measurement of tissue triglyceride levels—Lipids were extracted as described by Bligh and Dyer (Niwa et al, 1991). Samples were weighed then homogenized in PBS (100 mg/mL) and 1 mL of the sample was added to 3.75 mL of 1:2 (v/v) chloroform:methanol. Next, an additional 1.25 mL chloroform were added; subsequently, 1.25 mL $dH_2O$ were added to the solution. Samples were vortexed for 30 s between each addition. Samples were then centrifuged at 1100×g for 10 min at room temperature to give a two-phase solution (aqueous phase on top and organic phase below). The lower phase was collected with a glass Pasteur pipette with gentle positive pressure. This phase was then washed three times with $dH_2O$, and each time the upper phase was collected. Samples were then dried under Nitrogen gas at 60° C. and dissolved in tert-butyl alcohol:Triton X-100 (3:2). Triglycerides were then quantified colorimetrically as glycerol using a commercial enzymatic assay (Infinity™ Triglycerides, Fisher Diagnostics, Waltham, Mass.).

Quantitative real-time PCR—Total RNAs from mouse tissues were isolated with TRIzol200 (Invitrogen). Two µg of total RNA were reverse-transcribed using Superscript III (Invitrogen). Quantitative PCR analyses were performed on an Applied Biosystems Prism 7500 Sequence Detection System. Samples were analyzed in 25-µL reactions according to the standard protocol provided in the SyBR® Green PCR Master Mix (Applied Biosystems). All expression levels were normalized to the corresponding 18 S rRNA levels. Primer sequences can be found in Table 1.

TABLE 1

Quantitative real-time PCR primers

| Gene | Abbreviation | Forward primer | Reverse primer |
| --- | --- | --- | --- |
| 18 S rRNA | 18 S rRNA | GCAATTATTCCCCATG AACG (SEQ ID NO: 5) | GGCCTCACTAAACCATCCAA (SEQ ID NO: 6) |
| β-Actin | β-Actin | AGTGTGACGTTGACAT CCGTA (SEQ ID NO: 7) | GCCAGAGCAGTAATCTCCTTC T (SEQ ID NO: 8) |
| Peroxisome proliferator-activated receptor alpha | PPAR-α | ACAAGGCCTCAGGGTA CCA (SEQ ID NO: 9) | GCCGAAAGAAGCCCTTACAG (SEQ ID NO: 10) |

TABLE 1-continued

Quantitative real-time PCR primers

| Gene | Abbreviation | Forward primer | Reverse primer |
|---|---|---|---|
| Fatty acid synthase | FAS | GCTGCGGAAACTTCAGAAAAT (SEQ ID NO: 11) | AGAGACGTGTCACTCCTGGACTT (SEQ ID NO: 12) |
| Carnitine palmitoyltransferase I A | CPTIα | CACCAACGGGCTCATCTTCTA (SEQ ID NO: 13) | CAAAATGACCTAGCCTTCTATCGAA (SEQ ID NO: 14) |
| Diglyceride acyltransferase 1 | DGAT1 | GTGCCATCGTCTGCAAGATT (SEQ ID NO: 15) | CTGGATAGGATCCACCAGGA (SEQ ID NO: 16) |
| Diglyceride acyltransferase 2 | DGAT2 | GCGCTACTTCCGAGACTACTT (SEQ ID NO: 17) | GGGCCTTATGCCAGGAAACT (SEQ ID NO: 18) |
| Glycerol-3-phosphate acyltransferase 1 | GPAT1 | CATCCTCTTTTGCCACAACAT (SEQ ID NO: 19) | ACAGAATGTCTTTGCGTCCA (SEQ ID NO: 20) |
| Glycerol-3-phosphate acyltransferase 2 | GPAT2 | CTCCTGGTTGCAGAGGAGA (SEQ ID NO: 21) | AGCAGCTTTGCACTCAGATG (SEQ ID NO: 22) |
| Glycerol-3-phosphate acyltransferase 3 | GPAT3 | GGAGGATGAAGTGACCCAGA (SEQ ID NO: 23) | CCAGTTTTTGAGGCTGCTGT (SEQ ID NO: 24) |
| Glycerol-3-phosphate acyltransferase 4 | GPAT4 | TGTCTGGTTTGAGCGTTCTG (SEQ ID NO: 25) | TTCTGGGAAGATGAGGATGG (SEQ ID NO: 26) |
| Acylglycerolphosphate acyltransferase 1 | AGPAT1 | TAAGATGGCCTTCTACAACGGC (SEQ ID NO: 27) | CCATACAGGTATTTGACGTGGAG (SEQ ID NO: 28) |
| Acylglycerolphosphate acyltransferase 2 | AGPAT2 | CAGCCAGGTTCTACGCCAAG (SEQ ID NO: 29) | TGATGCTCATGTTATCCACGGT (SEQ ID NO: 30) |
| Acylglycerolphosphate acyltransferase 3 | AGPAT3 | CTGCTTGCCTACCTGAAGACC (SEQ ID NO: 31) | GATACGGCGGTATAGGTGCTT (SEQ ID NO: 32) |
| Acylglycerolphosphate acyltransferase 4 | AGPAT4 | CCAGTTTCTATGTCACCTGGTC (SEQ ID NO: 33) | GCAGAGTCTGGCATTGATCTTG (SEQ ID NO: 34) |
| Acylglycerolphosphate acyltransferase 5 | AGPAT5 | CACACGTACTCTATGCGCTAC (SEQ ID NO: 35) | AAGAAGAGCACCATGTTCTGG (SEQ ID NO: 36) |
| Acylglycerolphosphate acyltransferase 6 | AGPAT6 | AGCTTGATTGTCAACCTCCTG (SEQ ID NO: 37) | CCGTTGGTGTAGGGCTTGT (SEQ ID NO: 38) |
| Glucose-6-phosphatase | G6Pase | CGACTCGCTATCTCCAAGTGA (SEQ ID NO: 39) | GTTGAACCAGTCTCCGACCA (SEQ ID NO: 40) |
| Phosphoenolpyruvate carboxykinase | PEPCK | CTGCATAACGGTCTGGACTTC (SEQ ID NO: 41) | CAGCAACTGCCCGTACTCC (SEQ ID NO: 42) |
| C1q/TNF-related protein | CTRP3 | CATCTGGTGGCACCTGCTG (SEQ ID NO: 43) | TGACACAGGCAAAATGGGAG (SEQ ID NO: 44) |

Quantifying the rate of VLDL-triglyceride secretion—To measure hepatic TAG production rate, a separate cohort of HFD-fed mice (Tg and WT littermates) were given an intraperitoneal injection of 1000 mg/kg poloxamer 407 (Sigma-Aldrich, St. Louis, Mo.) in saline ~4 h into the light cycle, as described by Millar et al. (2005). P-407 is an inhibitor of lipoprotein lipase and it blocks TAG hydrolysis, thus allowing VLDL-TAG molecules to accumulate over time. This process allows for the calculation of hepatic VLDL-triglyceride secretion rates (Millar et al., 2005). Serum samples were collected at time 0, 1, 2, 6, and 24 h and analyzed for triglyceride concentration. The TAG production rate was calculated from the differences in plasma TAG levels over a given interval following P-407 injection.

Immunoblot analysis—Tissue and cell culture homogenates were prepared using Tissue Protein Extraction buffer (Pierce, Waltham, Mass.) supplemented with phosphatase and protease inhibitors (Calbiochem, Billerica, Mass.). Protein concentrations were determined using Bradford assay (ThermoFisher Scientific, Waltham, Mass.). 10 µg of protein from tissue lysates or 1 µL serum were loaded and separated on a 10% Bis-Tris NuPAGE gel (Invitrogen, Carlsbad, Calif.) and transferred to Protran BA8 nitrocellulose membranes (Whatman, Piscataway, N.J.). Membranes were blocked in 2% non-fat milk and probed with primary and HRP-conjugated secondary antibodies, and chemiluminescence signals were visualized via ECL (GE Healthcare, Piscataway, N.J.) with Multilmage III FuorChem ® Q (Alpha Innotech Corp, San Leandro, Calif.). Quantification of signal intensity was performed using Alphaview Software (Alpha Innotech Corp, San Leandro, Calif.). SeeBlue® Plus 2 molecular weight markers (Invitrogen, Carlsbad, Calif.) were used in all immunoblot analysis.

Protein purification—Recombinant full-length mouse CTRP3, containing a C-terminal FLAG epitope tag, was produced in HEK 293 mammalian cells (GripTite™ 293; Invitrogen, Carlsbad, Calif.) and purified as described previously (Peterson et al., 2010). The mammalian expression system ensures proper posttranslational modification and assembly of CTRP3 protein into its correct higher-order structure (Wong et al., 2002). Sufficient quantity of recombinant protein was purified from ~6 L of serum-free conditioned media to enable repeated administration into mice. Purified proteins were dialyzed against 20 mM Hepes buffer (pH 8.0) containing 135 mM NaCl in a 10 kDa cut-off Slide-A-Lyzer dialysis cassette (Pierce, Waltham, Mass.). Protein concentration was determined using a Coomassie Plus protein assay reagent (ThermoFisher Scientific, Waltham, Mass.) before samples were aliquoted and stored at −80° C. The purity of recombinant protein was judged to be >95% by Coomassie blue-stained gel.

Cell culture—Rat H4IIE hepatoma cells were maintained in Dulbecco's modified Eagle medium containing 10% newborn calf serum (Gemini Bio-products, West Sacramento, Calif.). All cell culture experiments were performed in triplicate. Free fatty acid/BSA (bovine serum albumin) conjugates were prepared as described previously (Listenberger et al., 2001). Briefly, a 20 mM solution of free fatty acids in 0.01 M NaOH were incubated at 70° C. for 30 min, and the fatty acid soaps were then complexed with 5% BSA in PBS at an 8:1 ratio of fatty acid to BSA. Conjugates were administered to cultured cells at concentrations indicated.

Fatty acid oxidation—To measure fatty acid oxidation, the protocol was adapted as described by Buzzai et al., in which oxidation of $[9,10-^3H]$-palmitic acid results in formation of $[^3H]$—$H_2O$ (Buzzai et al., 2005). In brief, cells were incubated for 2 h in serum-free DMEM containing 0.2% bovine serum albumin with recombinant CTRP3 (5 µg/mL) or vehicle buffer. Next, 0.2 µCi/mL $[9,10-^3H]$-palmitic acid (Moravek Biochemicals, Brea, Calif.) were added to the media, and cells were then incubated for 60 min. The tritiated palmitate was oxidized to $CO_2$ and $[^3H]$—$H_2O$. After incubation, the medium was transferred to a tube containing equal volume of chilled (4° C.) 10% trichloroacetic acid. Samples were mixed and incubated for 10 min at 4° C., then centrifuged for 30 min at 4° C. After centrifugation, 400 µL of the supernatant were collected and combined with 55 µL of 6N NaOH, then transferred to a Micro Bio-spin chromatography column (BioRad, Hercules, Calif.; Catalogue #732-6204), containing 0.5 g Dowex ion exchange resin (Sigma-Aldrich, St. Louis, Mo.; Product #217425). The $[^3H]$—$H_2O$ would be selectively retained by the resin while the hydrophobic, non-oxidized $[9, 10-^3H]$-palmitic acid in the supernatant would pass through the column. Bound $[^3H]$—$H_2O$ in the column was eluted with 1 mL $dH_2O$, and the elution was transferred to a liquid scintillation vial. The amount of $^3H$ radioactivity was determined with a Beckman Coulter counter (Beckman Coulter, Brea, Calif.; Model #LS6000SC). The amount of $[^3H]$—$H_2O$ collected indicates the extent of fatty acid oxidation.

Fatty acid uptake assay—H4IIE cells were washed twice in PBS and placed in stimulation media (0.1% BSA low glucose, fatty acid-free DMEM) at 37° C. and 5% $CO_2$ incubator for 2 h. Next, media was replaced with the same DMEM containing vehicle control, CTRP3 (5 µg/mL), or insulin (50 nM) and incubated overnight. Cells were transferred to a 37° C. water bath where 1 µCi/well (in a 24-well format) of $^3H$-labeled palmitate (dissolved previously for 1 h in the fatty-acid-free DMEM containing 0.1% BSA) was added for either 10, 30, or 60 s. Media was then aspirated out and cells were washed twice in cold PBS. Cells were lysed in 10% SDS and transferred to a scintillation vial. Radioactive counts were measured and normalized to protein concentration of cell lysate.

Fatty acid synthesis—Fatty acid synthesis was determined via measurement of $^3H$-acetate incorporation into cells as previously described (Pizer et al., 1996). Briefly, H4IIE hepatocytes were grown to confluence in a 24-well plate. Cells were then treated with vehicle buffer or CTRP3 (5 µg/mL) for 2 h. Next, cold acetic acid (100 mM) and 0.2 µCi/well $^3H$-acetic acid (American Radiolabeled Chemicals, Inc., St. Louis, Mo.) were added to the media. After 2 h incubation, cells were washed in PBS and lipids were extracted with varying amounts of chloroform/methanol and $MgCl_2$. Sample was re-suspended in a liquid scintillation vial and the amount of $^3H$ radioactivity was determined using a Beckman Coulter counter (Beckman Coulter, Brea, Calif.; Model #LS6000SC).

Recombinant protein injection—A separate cohort of 4-week-old C57BL/6 male mice was obtained from the Jackson Laboratory (Bar Harbor, Me.). After 1 week of acclimatization, the mice were placed on an HFD for 12 weeks. Mice were fasted for 8 h to obtain initial blood draw (2 h into dark cycle) and then allowed to recover for 72 h with ad libitum access to food. After recovery, initial body weight (considered day 0) was determined. Body weight was measured daily and CTRP3 (2 µg/g body weight) or vehicle buffer was administered daily via intraperitoneal route for the next 5 days. Injections were given at the same time each day (6 h into light cycle). After the fifth injection, food was immediately removed and mice were fasted for 8 h before final blood and tissue collections were performed.

CTRP3 gene expression from a mouse adipocyte cell line (3T3-L1 adipocyte)—Total RNA was extracted and reversed transcribed according to standard procedures (SABiosciences, Qiagen, Hilden, Del.). PCR primers for CTRP3 (Clqtnf3, NM_001204134.1; forward 5'-CATCTGGTGGCACCTGCTG-3' (SEQ ID NO: 43), reverse 5'-TGACACAGGCAAAATGGGAG-3' (SEQ ID NO: 44)) and 18S ribosomal RNA (Rn18s, NR_003278 primers; forward, 5'-GCAATTATTCCCCATGAACG-3' (SEQ ID NO: 5); reverse 5'-GGCCTCACTAAACCATCCAA-3' (SEQ ID NO: 6)) were used. The length of PCR products were assessed using microcapillary electrophoresis (Agilent Technologies, Santa Clara, Calif.) and only primers that did not amplify non-specific products and dimmers, were employed. A 10-fold dilution series of cDNA from isolated mouse adipose tissue was employed as a standard curve, and the reverse-transcription qPCR efficiency was determined for each gene and each treatment, as routinely performed. Only primers which displayed a coefficient of correlation greater than 0.99 and efficiencies between 95% and 108% were selected for the next qRT-PCR. Data is reported as copy number of CTRP3 relative to copy number of reference gene Rn18s.

Statistical analyses—Body weights, glucose and insulin tolerance test, and pre/post data from CTRP3 injection experiments were analyzed using a repeated-measures analysis of variance followed by Tukey post hoc analysis. All remaining statistical analyses were performed using a one-way analysis of variance. Statistical analyses were performed using GraphPad Prism 5 statistical software. Statistical significance was accepted at $p<0.05$. All data are reported as mean±standard error (SEM).

Abbreviations—Other abbreviations used herein may include: LCAD, long-chain acyl-CoA dehydrogenase; MCAD, medium-chain acyl-CoA dehydrogenase; COXII, cytochrome oxidase subunit II; CytoB, mitochondria cytochrome b; COX IV, cytochrome oxidase subunit IV; CPT1a, carnitine palmitoyltransferase 1a; ACAD, acyl-CoA dehydrogenase; ACOX, acyl-CoA oxidase; AGPAT, acyl glycerol phosphate acyltransferase; GPAT, glycerol phosphate acyltransferase; DGAT, diacylglycerol acyltransferase; FAS, fatty acid synthase; SREBP, sterol regulatory binding protein; PPAR-α, peroxisome proliferator-activated receptor alpha.

Generation of CTRP3 Tg Mouse Line

A Tg mouse model over-expressing FLAG epitope-tagged CTRP3 was generated. Because CTRP3 is a secreted protein and is normally expressed in multiple tissues and cell types in both mouse and human (Wong et al., 2008; Schaffler et al., 2003; Maeda et al., 2001), the Ctrp3 transgene was expressed using a ubiquitous promoter (FIG. 3A). As expected, the Tg mouse line has >5-fold higher circulating levels of CTRP3 over baseline serum levels found in wild-type mice (data not shown). At the mRNA level, Ctrp3 transgene was expressed in all tissues examined (FIG. 3B). At the protein level, FLAG-tagged CTRP3 was detected in the liver, heart, muscle, and kidney, but not in brain or adipose tissue (FIG. 3C).

Body Weight Gain and Energy Expenditure in Response to HFD

Figure 4:
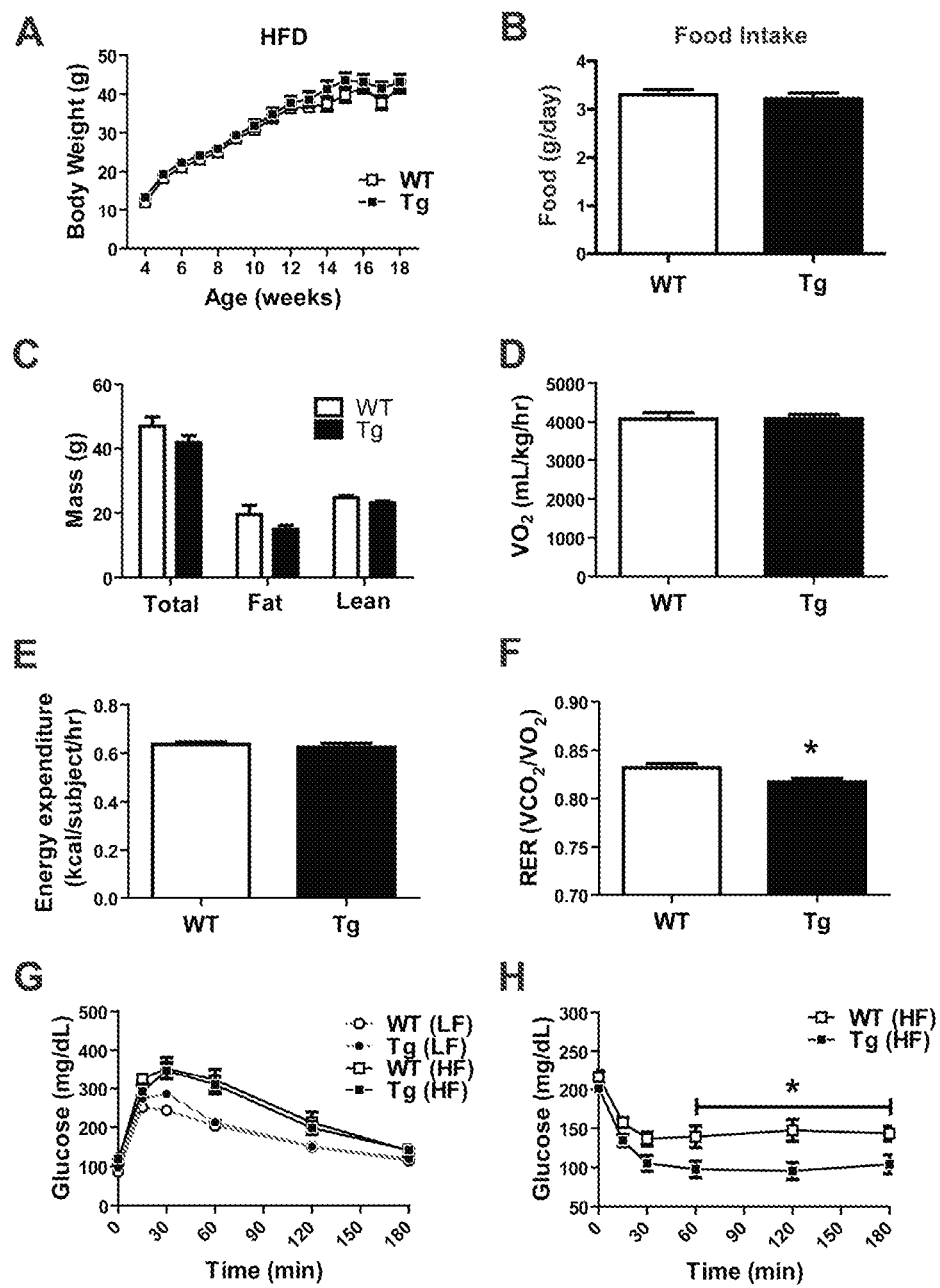
Figure 5:
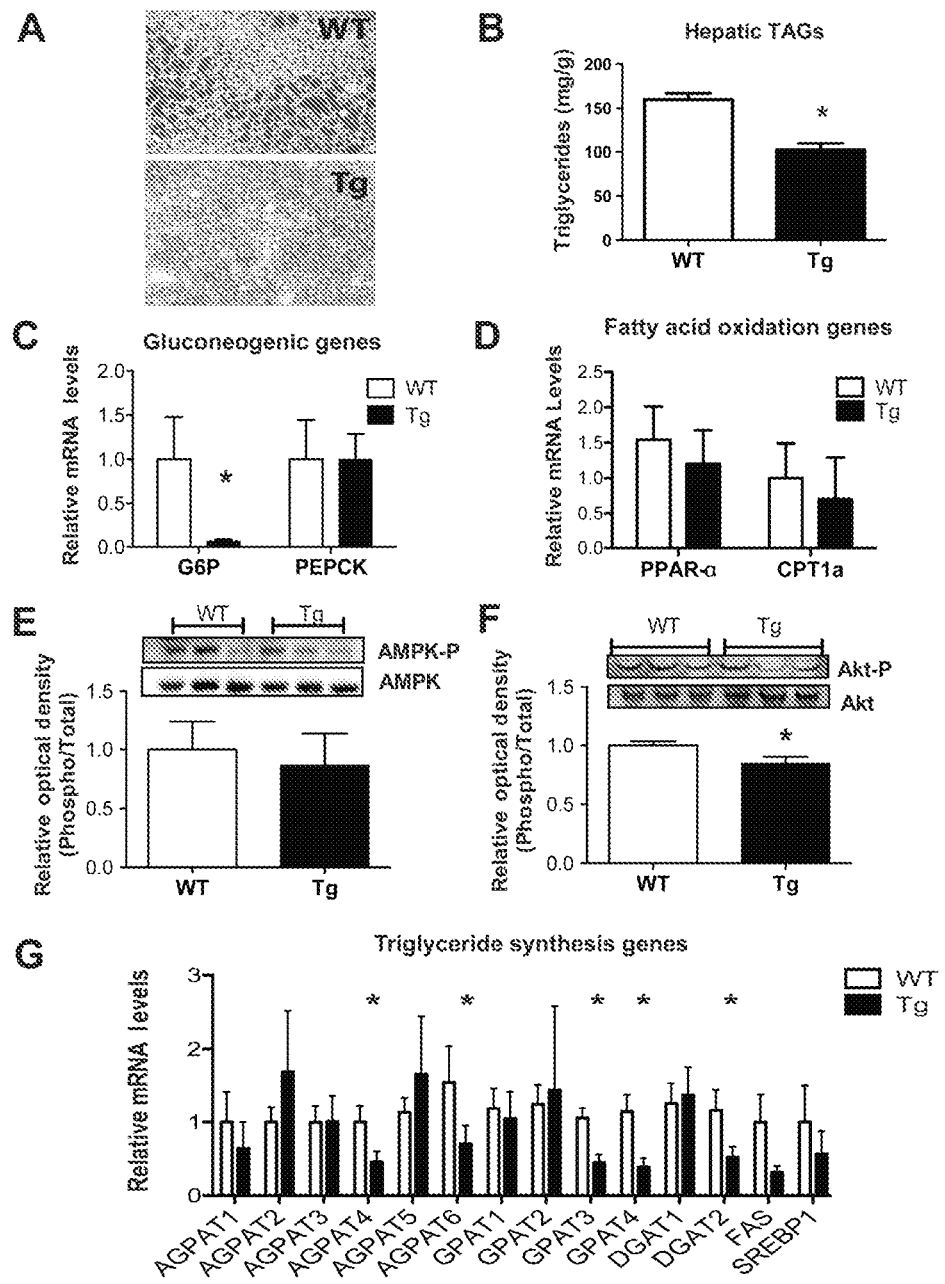

The CTRP3 Tg mice developed normally with no obvious phenotype. Body weight gains on LFD (data not shown) and HFD (FIG. 4B) over a period of 14 weeks were indistinguishable between Tg and WT mice. No differences were observed in food intake, total fat, or lean body mass between Tg and WT mice fed an LFD (data not shown) or an HFD (FIGS. 4B-C). Oxygen consumption (indicative of basal metabolic rate) and energy expenditure were also similar between HFD-fed Tg and WT mice (FIGS. 4D, E). However, a modest, but significant, reduction in respiratory exchange ratio (RER) was observed in Tg mice relative to littermate controls (FIG. 4F), indicating a greater utilization of fatty acids as fuel source. No differences in glucose tolerance were observed between Tg and WT mice fed an LFD (data not shown) or an HFD (FIG. 4G), nor were there any differences in the magnitude of insulin secretion between the two groups in response to glucose injection (data not shown). When subjected to insulin tolerance test, however, Tg mice on an HFD clearly demonstrated greater insulin sensitivity relative to WT controls, as indicated by a sustained and significantly greater reduction in blood glucose levels after insulin administration (FIG. 4H).

Fasting Serum Analysis of HFD-fed Tg and WT Mice

Serum levels of hormones and metabolites are tightly linked to metabolic state. Therefore, blood chemistry analysis was performed on WT and Tg mice. Improvements in fasting glucose, insulin, glucagon, NEFA non-esterified free fatty acid), TAGs, or adiponectin levels following HFD in Tg mice relative to control littermates were not observed (Table 2). However, a substantial reduction in serum cholesterol (22%), LDL (31%), and HDL (13%) levels in Tg mice when compared to littermate controls were observed (Table 2). Low-grade chronic inflammation, reflected in elevated plasma levels of TNF-α, is frequently associated with obesity (Hotamisligil, 2006). Strikingly, a marked reduction (66%) in the circulating levels of TNF-α in Tg mice relative to controls was also observed (Table 2).

TABLE 2

Blood chemistry analysis of WT and Tg mice.

| Serum marker | WT | Tg | p-Value |
|---|---|---|---|
| Insulin (ng/mL) | 1.3 ± 0.18 | 1.7 ± 0.18 | ns |
| Glucose (mg/dL) | 109.6 ± 6.5 | 101.9 ± 10.1 | ns |
| Glucagon (pM) | 13.3 ± 0.32 | 13.8 ± 0.26 | ns |
| Adiponectin (μg/mL) | 12.5 ± 1.3 | 13.0 ± 1.3 | ns |
| TNF-α (pg/mL) | 6.4 ± 2.0 | 2.2 ± 0.3 | p < 0.01 |
| Cholesterol (total; mg/dL) | 138.0 ± 8.6 | 108.5 ± 6.3 | p < 0.01 |
| Low-density lipoprotein (LDL) | 67.2 ± 6.2 | 46.4 ± 3.9 | p < 0.01 |
| High-density lipoprotein (HDL) | 59.4 ± 2.3 | 51.5 ± 2.8 | p < 0.01 |
| NEFA (mEq/L) | 0.89 ± 0.06 | 0.97 ± 0.07 | ns |
| Triglycerides (mg/dL) | 41.9 ± 3.6 | 43.9 ± 3.2 | ns |

Reduced Expression of Lipid Synthesis Genes and Hepatic TAG Levels in Tg Mice When liver sections were stained with oil red O to detect the presence of neutral lipids, dramatic differences were observed between Tg and WT mice (FIG. 5A), clearly indicating a striking resistance of Tg mice to developing hepatic steatosis in response to HFD. Quantification of hepatic TAG levels confirmed a 38% reduction in TAG levels in Tg mice relative to control littermates (FIG. 5B). Expression of hepatic glucose-6-phosphatase (G6pase), a key gluconeogenic enzyme, was reduced by 90% in Tg mice (FIG. 5C), confirming a previous study based on recombinant CTRP3 protein administration (Peterson et al., 2010). Expression of hepatic Ppar-α, a major transcriptional regulator of fat oxidation genes, was not changed between Tg and WT mice (FIG. 5D), nor were there any differences in the expression of genes directly involved in fat oxidation (e.g., Cpt1a, Acoxs, Acads) (FIG. 5D and data not shown). As observed following acute CTRP3 protein administration (Peterson et al., 2010), no significant differences in the phosphorylation levels of AMPKα (AMP-activated protein kinase α) were detected in the liver of Tg and WT mice (FIG. 5E). In contrast to acute recombinant protein administration (Peterson et al., 2010), when plasma CTRP3 protein was chronically elevated as in Tg mice, a modest reduction in hepatic Akt phosphorylation was observed (FIG. 5F). Importantly, the expression levels of a number of genes involved in TAG synthesis were substantially reduced in the liver of Tg mice relative to control littermates (FIG. 5G).

CTRP3 Reduces Fatty Acid Synthesis and Neutral Lipid Accumulation in Cultured Hepatoma Cells A cell culture system was used to confirm the in vivo findings and to demonstrate that CTRP3 protein directly regulates lipid metabolism in liver cells. When rat H4IIE hepatocytes were co-incubated overnight with recombinant CTRP3 protein and 200 nM oleic acid conjugated to bovine serum albumin to promote lipid loading, the amount of neutral lipids (mainly TAGs) accumulated in cells was significantly reduced (~20%) compared to vehicle-treated controls (FIG. 6A). Whereas the uptake of exogenous fatty acids was not affected by CTRP3 protein treatment (FIG. 6C), de novo fatty acid synthesis, as measured by radiolabeled acetate incorporation, was suppressed (~22%) in H4IIE cells treated with CTRP3 protein (FIG. 6B).

Measurement of VLDL-TAG Export in Tg and WT Mice

To assess the rate and magnitude of VLDL-TAG secretion from the liver, a separate cohort of HFD-fed mice was injected with poloxamer 407, an inhibitor of lipoprotein lipase that blocks VLDL-TAG hydrolysis and clearance (Millar et al., 2005). Tg mice given poloxamer 407 had a significantly reduced TAG accumulation in the blood (FIG. 7A) and a reduced rate of TAG secretion from the liver (FIG. 7B). As TAGs are mainly secreted from the liver as VLDL particles, these results suggest that the reduction in hepatic TAG accumulation in Tg mice is indeed due to the suppression of TAG synthesis (FIG. 5) and not caused by increased hepatic VLDL-TAG export.

Short Term Administration of Recombinant CTRP3

Figure 8:
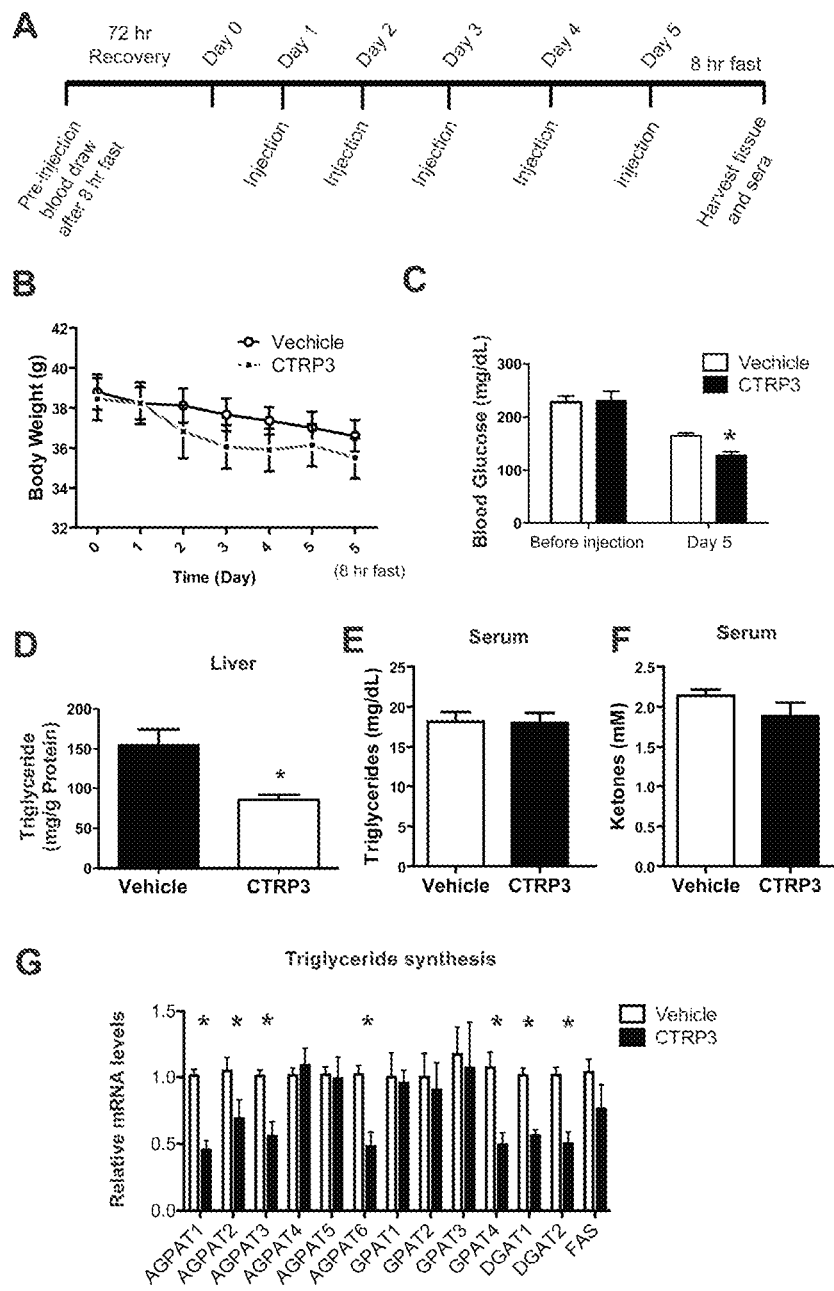

Next, a short-term recombinant protein supplementation study was conducted to further ensure that the remarkable phenotype observed in the liver of Tg mice is directly attributable to elevated plasma CTRP3 levels and not due to potential secondary effects of transgene overexpression. To address this issue, a separate cohort of WT mice was placed on an HFD for 12 weeks to induce obesity and the development of fatty liver. DIO mice have similar starting body weights to one another and were given a daily injection of vehicle or recombinant CTRP3 protein (2 μg/g body weight) for 5 consecutive days as outlined (FIG. 8A). Both vehicle- and CTRP3-treated DIO mice lost ~2 g of body weight during the course of the experiment (FIG. 8B). Consistent with the previous findings, in which a single dose of CTRP3 injection acutely reduces blood glucose levels (Peterson et al., 2010), DIO mice that received a 5-day injection also had a 22% reduction in blood glucose levels (FIG. 8C). Strikingly, recombinant protein administration over 5 days resulted in a 43% reduction in hepatic TAGs (vehicle, 155.2+19.4 mg/g vs. CTRP3, 88.6+6.3 mg/g). Serum levels of TAGs and ketones were not different between the two groups of DIO mice (FIGS. 8E, F). Serum ketone levels reflect the extent of hepatic fat oxidation; thus, unchanged ketone levels provide further support that hepatic fat oxidation may not be responsible for the reduction of TAG content in the liver of mice injected with recombinant protein. As with the Tg mice, reduced hepatic TAGs in CTRP3-injected DIO mice was due to major reduction in the expression of most hepatic enzyme genes involved in TAG synthesis (FIG. 8G).

Recombinant CTRP3 Reduces Ethanol-induced Damage in Cultured Hepatoma Cells

It had previously been demonstrated that CTRP3 has a direct effect on the liver. To establish that CTRP3 has a hepatic-protective effect, cultured hepatoma cells were treated with recombinant CTRP3 protein to see if they were resistant to ethanol-induced cell damage or death. Rat H4IIE hepatocytes were treated overnight (18 hrs) with ethanol (100 mM) and recombinant CTRP3 protein (5 μg/ml). Treatment with CTRP3 significantly reduced the percentage of dead cells (as determined by counting trypan blue positive cells; FIG. 9).

CTRP3 Gene Expression is Reduced from Ethanol-exposed Adipocytes

Adipose tissue is an important target for ethanol action. For example, Xu et.al. (2003) demonstrated that chronic ethanol feeding decreases the serum concentration of another C1q TNF superfamily adipokine, adiponectin. Therefore, the effect of ethanol exposure on the gene expression of CTRP3 from a mouse adipocyte cell line (3T3-L1 adipocyte) was tested. Results showed that CTRP3 levels were suppressed by ethanol (FIG. 10). These results show that exogenous CTRP3 can be used to restore suppressed CTRP3 levels as a treatment for alcoholic fatty liver disease.

Discussion

In the present study, multiple lines of evidence were provided to establish the role of CTRP3 in regulating hepatic lipid metabolism. Tg mice with elevated plasma levels of CTRP3 are strikingly resistant to the development of HFD-induced hepatic steatosis, independent of other metabolic parameters such as food intake, body weight, adiposity, and energy expenditure. Without wishing to be bound to any one particular theory, it is believed that three possible mechanisms involving production and/or removal of TAG could account for the marked reduction in liver TAG content in Tg mice on an HFD: 1) increased hepatic fat oxidation; 2) increased TAG export from liver in the form of VLDL-TAG particles; 3) decreased synthesis of TAG in liver. The in vivo and in vitro data suggest that CTRP3-mediated suppression of TAG synthesis is primarily responsible for reduced hepatic TAG content seen in Tg mice.

In liver, TAG is synthesizes via the glycerol phosphate pathway (Bell and Coleman, 1980) through sequential acylation of glycerol-3 phosphate, lysophosphatidic acid, and diacylglycerol by multiple isoforms of GPAT, AGPAT, and DGAT enzymes (Takeuchi and Reue, 2009; Yen et al., 2008). It has been shown that the expression of these enzymes in liver are significantly suppressed in HFD-fed CTRP3 Tg and wild-type DIO mice administered recombinant CTRP3, thus contributing to reduced hepatic lipid content seen in these animals relative to controls. Remarkably, daily supplementation of recombinant protein for 5 days is sufficient to markedly reduce hepatic TAG levels in wild-type DIO mice, confirming that the improved liver phenotype in Tg mice is due to elevated plasma CTRP3 levels and not a consequence of secondary effects of transgene over-expression. It was also noted that serum adiponectin levels were not different between Tg and WT mice, indicating that decreased hepatic TAG content is unlikely due to adiponectin, an adipokine known to alleviate diet-induced hepatic steatosis in mice, largely by increasing hepatic fat oxidation (Xu et al., 2003; Yamauchi et al., 2001).

A very modest improvement in insulin sensitivity was observed, as judged by insulin but not glucose tolerance test, in HFD-fed CTRP3 Tg mice. Excessive fat deposition in hepatocytes, a hallmark of steatosis, is frequently associated with hepatic insulin resistance (Kotronen et al., 2008; Kotronen et al., 2007; Sunny et al., 2011; Samuel et al., 2010). Whether hepatic steatosis causes or is a consequence of insulin resistance is a hotly debated issue (Cohen et al., 2011; Samuel et al., 2010; Farese et al., 2012; Nagle et al., 2009). Two recent studies using transgenic over-expression of diacylglycerol O-acyltransferase 2 (DGAT2) in mouse liver to alter hepatic lipid content have yielded contradictory results on hepatic insulin sensitivity (Jornayvaz et al., 2011; Monetti et al., 2007). Also, several other mouse models, with reduced fatty acid synthesis (Chakravarthy et al., 2005), mobilization (Brown et al., 2010; Hoy et al., 2011; Minehira et al., 2008; Wu et al., 2011), or oxidation (Monsenego et al., 2011), developed hepatic steatosis without accompanying insulin resistance. Give the very modest improvements in insulin sensitivity seen in the HFD-fed CTRP3 Tg mice compared to littermate controls, it is unclear whether this modest phenotype is due to reduced hepatic lipid content. The mechanistic link between hepatic steatosis and insulin resistance remains to be fully established (Nagle et al., 2009).

It has previously been shown that a single injection of recombinant CTRP3 acutely lowered blood glucose levels in WT and genetically obese (ob/ob) mice (Peterson et al., 2010). The CTRP3-mediated suppression of hepatic gluconeogenesis is correlated with the activation of protein kinase B/Akt. In contrast, chronic over-expression of CTRP3 in Tg mice resulted in decreased Akt activation despite a marked suppression of hepatic gluconeogenic gene (G6Pase) expression (FIGS. 5C, F). This suggests that CTRP3 can inhibit hepatic G6Pase expression independent of Akt signaling. Although chronic over-expression of CTRP3 in Tg mice did not lower fasting blood glucose levels (Table 2), short-term administration of recombinant CTRP3 (one injection per day for 5 days) significantly reduced fasting blood glucose levels in DIO mice (FIG. 8C). The glucose-lowering seen in DIO mice is similar to WT and ob/ob mice acutely injected with recombinant CTRP3 (Peterson et al., 2010). Without wishing to be bound to any one particular theory, it is believed that because blood glucose levels are tightly regulated, chronic over-expression of CTRP3 in Tg mice may result in homeostatic compensation to prevent hypoglycemia induced by CTRP3. This may account for the lack of differences in fasting blood glucose levels between WT and Tg mice.

Interestingly, a decrease in the circulating levels of TNF-α in Tg mice was observed, likely reflecting a dampening of chronic low-grade systemic inflammation associated with high-fat feeding (Hotamisligil, 2006; Gregor and Hotamisligil, 2011). The in vivo observation is consistent with a previous study demonstrating the ability of recombinant CTRP3 protein to inhibit TNF-α release from primary human macrophages isolated from healthy donors (Kopp et al., 2010). Mice lacking TNF-α or its receptors are protected from obesity-induced insulin resistance (Uysal et al., 1997). Therefore, without wishing to be bound to any one particular theory, it is believed that lower serum levels of TNF-α seen in CTRP3 Tg mice may contribute to the modest improvement in systemic insulin sensitivity. In addition, the finding that TNF-α was reduced in CTRP3 Tg mice suggests that CTRP3 prevents M1 polarization of macrophages and can be used in preventing or treating diet or alcohol-induced liver inflammation.

A reversal or improvement in hepatic steatosis is possible through lifestyle modifications such as reduced energy intake and/or weight loss (Petersen et al., 2005), as well as gastric bypass surgery (Luyckx et al., 1998). However, lifestyle changes are often difficult to sustain, necessitating alternative treatment options. One way to reduce liver TAG content is by decreasing TAG synthesis. Previous proof-of-principle studies using siRNA targeting DGAT2 or small molecule inhibitor of GPAT or DGAT1 have demonstrated the feasibility of attenuating hepatic steatosis in rodent (Choi et al., 2007; Kuhajda et al., 2011; Cao et al., 2011). It is shown herein that increasing plasma CTRP3 levels can significantly suppress TAG synthesis through downregulation of TAG synthesis genes (i.e., Agpat, Gpat, and Dgat), thereby improving the fatty liver phenotype in mice without affecting food intake and body weight. This highlights the potential therapeutic value of recombinant CTRP3 protein supplementation in mitigating NAFLD in humans. Given that siRNA or small molecule inhibitor of enzyme often has unintended off-target effects (Jackson et al., 2006; Fedorov et al., 2006; Fabian et al., 2005), the use of recombinant protein therapy to treat obesity-linked fatty liver may prove to be advantageous.

In sum, novel insights are provided into the metabolic function of CTRP3 and reveal, for the first time, its protective function in liver in response to excess caloric intake. The data show the utility of recombinant CTRP3 as a potential protein therapeutic for treating obesity-associated fatty liver disease.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Akiyama, H., S. Furukawa, S. Wakisaka, and T. Maeda. 2006. Cartducin stimulates mesenchymal chondroprogenitor cell proliferation through both extracellular signal-regulated kinase and phosphatidylinositol 3-kinase/Akt pathways. Febs J 273: 2257-2263;

Akiyama, H., S. Furukawa, S. Wakisaka, and T. Maeda. 2007. CTRP3/cartducin promotes proliferation and migration of endothelial cells. Mol Cell Biochem 304: 243-248;

Akiyama, H., S. Furukawa, S. Wakisaka, and T. Maeda. 2009. Elevated expression of CTRP3/cartducin contributes to promotion of osteosarcoma cell proliferation. Oncol Rep 21: 1477-1481;

Baichwal and Sugden, In: Gene Transfer. Kucherlapati R, ed., N.Y., Plenum Press, pp. 117-148, 1986;

Bell, R. M., and R. A. Coleman. 1980. Enzymes of glycerolipid synthesis in eukaryotes. Annu Rev Biochem 49: 459-487;

Brown, J. M., J. L. Betters, C. Lord, Y. Ma, X. Han, K. Yang, H. M. Alger, J. Melchior, J. Sawyer, R. Shah, M. D. Wilson, X. Liu, M. J. Graham, R. Lee, R. Crooke, G. I. Shulman, B. Xue, H. Shi, and L. Yu. 2010. CGI-58 knockdown in mice causes hepatic steatosis but prevents diet-induced obesity and glucose intolerance. J Lipid Res 51: 3306-3315;

Browning, J. D., and J. D. Horton. 2004. Molecular mediators of hepatic steatosis and liver injury. J Clin Invest 114: 147-152;

Buzzai, M., D. E. Bauer, R. G. Jones, R. J. Deberardinis, G. Hatzivassiliou, R. L. Elstrom, and C. B. Thompson. 2005. The glucose dependence of Akt-transformed cells can be reversed by pharmacologic activation of fatty acid beta-oxidation. Oncogene 24: 4165-4173;

Cao, J., Y. Zhou, H. Peng, X. Huang, S. Stahler, V. Suri, A. Qadri, T. Gareski, J. Jones, S. Hahm, M. Perreault, J. McKew, M. Shi, X. Xu, J. F. Tobin, and R. E. Gimeno. 2011. Targeting Acyl-CoA:diacylglycerol acyltransferase 1 (DGAT1) with small molecule inhibitors for the treatment of metabolic diseases. J Biol Chem 286: 41838-41851;

Chakravarthy, M. V., Z. Pan, Y. Zhu, K. Tordjman, J. G. Schneider, T. Coleman, J. Turk, and C. F. Semenkovich. 2005. "New" hepatic fat activates PPARalpha to maintain glucose, lipid, and cholesterol homeostasis. Cell Metab 1: 309-322;

Choi, C. S., D. B. Savage, A. Kulkarni, X. X. Yu, Z. X. Liu, K. Morino, S. Kim, A. Distefano, V. T. Samuel, S. Neschen, D. Zhang, A. Wang, X. M. Zhang, M. Kahn, G. W. Cline, S. K. Pandey, J. G. Geisler, S. Bhanot, B. P. Monia, and G. I. Shulman. 2007. Suppression of diacylglycerol acyltransferase-2 (DGAT2), but not DGAT1, with antisense oligonucleotides reverses diet-induced hepatic steatosis and insulin resistance. J Biol Chem 282: 22678-22688;

Clark, 2006, J. Clin. Gastroenterol. 40(Suppl 1):S5-S10;

Cohen, J. C., J. D. Horton, and H. H. Hobbs. 2011. Human fatty liver disease: old questions and new insights. Science 332: 1519-1523;

Enomoto, T., K. Ohashi, R. Shibata, A. Higuchi, S. Maruyama, Y. Izumiya, K. Walsh, T. Murohara, and N. Ouchi. 2011. Adipolin/Clqdc2/CTRP12 functions as an adipokine that improves glucose metabolism. J Biol Chem 286: 34552-34558; Evan et al., Molecular and Cellular Biology, 5:3610-3616 (1985);

Fabian, M. A., W. H. Biggs, 3rd, D. K. Treiber, C. E. Atteridge, M. D. Azimioara, M. G. Benedetti, T. A. Carter, P. Ciceri, P. T. Edeen, M. Floyd, J. M. Ford, M. Galvin, J. L. Gerlach, R. M. Grotzfeld, S. Herrgard, D. E. Insko, M. A. Insko, A. G. Lai, J. M. Lelias, S. A. Mehta, Z. V. Milanov, A. M. Velasco, L. M. Wodicka, H. K. Patel, P. P. Zarrinkar, and D. J. Lockhart. 2005. A small molecule-kinase interaction map for clinical kinase inhibitors. Nat Biotechnol 23: 329-336;

Farese, R. V., Jr., R. Zechner, C. B. Newgard, and T. C. Walther. 2012. The problem of establishing relationships between hepatic steatosis and hepatic insulin resistance. Cell Metab 15: 570-573;

Fedorov, Y., E. M. Anderson, A. Birmingham, A. Reynolds, J. Karpilow, K. Robinson, D. Leake, W. S. Marshall, and A. Khvorova. 2006. Off-target effects by siRNA can induce toxic phenotype. RNA 12: 1188-1196;

Field et al., Mol. Cell. Biol., 8:2159-2165 (1988);

Gregor, M. F., and G. S. Hotamisligil. 2011. Inflammatory mechanisms in obesity. Annu Rev Immunol 29: 415-445;

Hofmann, C., N. Chen, F. Obermeier, G. Paul, C. Buchler, A. Kopp, W. Falk, and A. Schaffler. 2011. Clq/TNF-related protein-3 (CTRP-3) is secreted by visceral adipose tissue and exerts antiinflammatory and antifibrotic effects in primary human colonic fibroblasts. Inflamm Bowel Dis 17: 2462-2471;

Hopp et al., BioTechnology, 6:1204-1210 (1988);

Hotamisligil, G. S. 2006. Inflammation and metabolic disorders. Nature 444: 860-867;

Hoy, A. J., C. R. Bruce, S. M. Turpin, A. J. Morris, M. A. Febbraio, and M. J. Watt. 2011. Adipose triglyceride lipase-null mice are resistant to high-fat diet-induced insulin resistance despite reduced energy expenditure and ectopic lipid accumulation. Endocrinology 152: 48-58;

Jackson, A. L., J. Burchard, J. Schelter, B. N. Chau, M. Cleary, L. Lim, and P. S. Linsley. 2006. Widespread siRNA "off-target" transcript silencing mediated by seed region sequence complementarity. RNA 12: 1179-1187;

Jornayvaz, F. R., A. L. Birkenfeld, M. J. Jurczak, S. Kanda, B. A. Guigni, D. C. Jiang, D. Zhang, H. Y. Lee, V. T. Samuel, and G. I. Shulman. 2011. Hepatic insulin resistance in mice with hepatic overexpression of diacylglycerol acyltransferase 2. Proc Natl Acad Sci USA 108: 5748-5752;

Kim, J. K., J. J. Fillmore, Y. Chen, C. Yu, I. K. Moore, M. Pypaert, E. P. Lutz, Y. Kako, W. Velez-Carrasco, I. J. Goldberg, J. L. Breslow, and G. I. Shulman. 2001. Tissue-specific overexpression of lipoprotein lipase causes tissue-specific insulin resistance. Proc Natl Acad Sci USA 98: 7522-7527;

Kopp, A., M. Bala, C. Buechler, W. Falk, P. Gross, M. Neumeier, J. Scholmerich, and A. Schaffler. 2010. Clq/TNF-related protein-3 represents a novel and endogenous lipopolysaccharide antagonist of the adipose tissue. Endocrinology 151: 5267-5278;

Kopp, A., M. Bala, J. Weigert, C. Buchler, M. Neumeier, C. Aslanidis, J. Scholmerich, and A. Schaffler. 2010. Effects of the new adiponectin paralogous protein CTRP-3 and of LPS on cytokine release from monocytes of patients with type 2 diabetes mellitus. Cytokine 49: 51-57;

Kotronen, A., A. Seppala-Lindroos, R. Bergholm, and H. Yki-Jarvinen. 2008. Tissue specificity of insulin resistance in humans: fat in the liver rather than muscle is associated with features of the metabolic syndrome. Diabetologia 51: 130-138;

Kotronen, A., S. Vehkavaara, A. Seppala-Lindroos, R. Bergholm, and H. Yki-Jarvinen. 2007. Effect of liver fat on insulin clearance. Am J Physiol Endocrinol Metab 293: E1709-1715;

Kuhajda, F. P., S. Aja, Y. Tu, W. F. Han, S. M. Medghalchi, R. El Meskini, L. E. Landree, J. M. Peterson, K. Daniels, K. Wong, E. A. Wydysh, C. A. Townsend, and G. V. Ronnett. 2011. Pharmacological glycerol-3-phosphate acyltransferase inhibition decreases food intake and adiposity and increases insulin sensitivity in diet-induced obesity. Am J Physiol Regul Integr Comp Physiol 301: R116-130;

Lazo, M., and J. M. Clark. 2008. The epidemiology of nonalcoholic fatty liver disease: a global perspective. Semin Liver Dis 28: 339-350;

Listenberger, L. L., D. S. Ory, and J. E. Schaffer. 2001. Palmitate-induced apoptosis can occur through a ceramide-independent pathway. J Biol Chem 276: 14890-14895;

Lutz-Freyermuth et al., Proc. Natl. Acad. Sci. USA, 87:6393-6397 (1990); Luyckx, F. H., C. Desaive, A. Thiry, W. Dewe, A. J. Scheen, J. E. Gielen, and P. J. Lefebvre. 1998. Liver abnormalities in severely obese subjects: effect of drastic weight loss after gastroplasty. Int J Obes Relat Metab Disord 22: 222-226;

Maeda, T., M. Abe, K. Kurisu, A. Jikko, and S. Furukawa. 2001. Molecular cloning and characterization of a novel gene, CORS26, encoding a putative secretory protein and its possible involvement in skeletal development. J Biol Chem 276: 3628-3634;

Maeda, T., A. Jikko, M. Abe, T. Yokohama-Tamaki, H. Akiyama, S. Furukawa, M. Takigawa, and S. Wakisaka. 2006. Cartducin, a paralog of Acrp30/adiponectin, is induced during chondrogenic differentiation and promotes proliferation of chondrogenic precursors and chondrocytes. J Cell Physiol 206: 537-544; Maeda, T., and S. Wakisaka. 2010. CTRP3/cartducin is induced by transforming growth factor-beta1 and promotes vascular smooth muscle cell proliferation. Cell Biol Int 34: 261-266;

Martin et al., Science, 255:192-194 (1992);

Millar, J. S., D. A. Cromley, M. G. McCoy, D. J. Rader, and J. T. Billheimer. 2005. Determining hepatic triglyceride production in mice: comparison of poloxamer 407 with Triton WR-1339. J Lipid Res 46: 2023-2028;

Minehira, K., S. G. Young, C. J. Villanueva, L. Yetukuri, M. Oresic, M. K. Hellerstein, R. V. Farese, Jr., J. D. Horton, F. Preitner, B. Thorens, and L. Tappy. 2008. Blocking VLDL secretion causes hepatic steatosis but does not affect peripheral lipid stores or insulin sensitivity in mice. J Lipid Res 49: 2038-2044;

Monetti, M., M. C. Levin, M. J. Watt, M. P. Sajan, S. Marmor, B. K. Hubbard, R. D. Stevens, J. R. Bain, C. B. Newgard, R. V. Farese, Sr., A. L. Hevener, and R. V. Farese, Jr. 2007. Dissociation of hepatic steatosis and insulin resistance in mice overexpressing DGAT in the liver. Cell Metab 6: 69-78;

Monsenego, J., A. Mansouri, M. Akkaoui, V. Lenoir, C. Esnous, V. Fauveau, V. Tavernier, J. Girard, and C. Prip-Buus. 2011. Enhancing liver mitochondrial fatty acid oxidation capacity in obese mice improves insulin sensitivity independently of hepatic steatosis. J Hepatol 56: 632-639;

Nagle, C. A., E. L. Klett, and R. A. Coleman. 2009. Hepatic triacylglycerol accumulation and insulin resistance. J Lipid Res 50 Suppl: S74-79;

Nicolas and Rubinstein, In: Vectors: A survey of molecular cloning vectors and their uses, Rodriguez and Denhardt, eds., Stoneham: Butterworth, pp. 494-513, 1988;

Niwa, H., K. Yamamura, and J. Miyazaki. 1991. Efficient selection for high-expression transfectants with a novel eukaryotic vector. Gene 108: 193-199;

Paborsky et al., Protein Engineering, 3(6):547-553 (1990);

Peterson, J. M., Z. Wei, and G. W. Wong. 2010. C1q/TNF-related Protein-3 (CTRP3), a Novel Adipokine That Regulates Hepatic Glucose Output. J Biol Chem 285: 39691-39701;

Peterson, J. M., S. Aja, Z. Wei, and G. W. Wong. 2012. C1q/TNF-related protein-1 (CTRP1) enhances fatty acid oxidation via AMPK activation and ACC inhibition. J Biol Chem 287: 1576-1587;

Petersen, K. F., S. Dufour, D. Befroy, M. Lehrke, R. E. Hendler, and G. I.

Shulman. 2005. Reversal of nonalcoholic hepatic steatosis, hepatic insulin resistance, and hyperglycemia by moderate weight reduction in patients with type 2 diabetes. Diabetes 54: 603-608;

Pizer, E. S., C. Jackisch, F. D. Wood, G. R. Pasternack, N. E. Davidson, and F. P. Kuhajda. 1996 Inhibition of fatty acid synthesis induces programmed cell death in human breast cancer cells. Cancer Res 56: 2745-2747;

Postic, C., and J. Girard. 2008. Contribution of de novo fatty acid synthesis to hepatic steatosis and insulin resistance: lessons from genetically engineered mice. J Clin Invest 118: 829-838;

Queen, et al., Immunol. Rev. 89:49-68, (1986);

Samuel, V. T., K. F. Petersen, and G. I. Shulman 2010. Lipid-induced insulin resistance: unravelling the mechanism. Lancet 375: 2267-2277; Schaffler, A., A. Ehling, E. Neumann, H. Herfarth, G. Paul, I. Tamer, S. Gay, J. Scholmerich, and U. Muller-Ladner. 2003. Genomic organization, promoter, amino acid sequence, chromosomal localization, and expression of the human gene for CORS-26 (collagenous repeat-containing sequence of 26-kDa protein). Biochim Biophys Acta 1630: 123-129;

Seldin, M. M., J. M. Peterson, M. S. Byerly, Z. Wei, and G. W. Wong. 2012. Myonectin (CTRP 15), a novel myokine that links skeletal muscle to systemic lipid homeostasis. J Biol Chem 287: 11968-11980;

Skinner et al., J. Biol. Chem., 266:15163-15166 (1991);

Szczepaniak, L. S., P. Nurenberg, D. Leonard, J. D. Browning, J. S. Reingold, S. Grundy, H. H. Hobbs, and R. L. Dobbins. 2005. Magnetic resonance spectroscopy to measure hepatic triglyceride content: prevalence of hepatic steatosis in the general population. Am J Physiol Endocrinol Metab 288: E462-468;

Sunny, N. E., E. J. Parks, J. D. Browning, and S. C. Burgess. 2011. Excessive hepatic mitochondrial TCA cycle and gluconeogenesis in humans with nonalcoholic fatty liver disease. Cell Metab 14: 804-810;

Takeuchi, K., and K. Reue. 2009. Biochemistry, physiology, and genetics of GPAT, AGPAT, and lipin enzymes in triglyceride synthesis. Am J Physiol Endocrinol Metab 296: E1195-1209;

Temin, In: Gene Transfer, Kucherlapati, R. ed. New York. Plenum Press, pp. 149-188, 1986;

Thompson J. D. et al., Nucleic Acids Res. 22:4673-4680 (1994);

Treeprasertsuk, S., S. Leverage, L. A. Adams, K. D. Lindor, J. St Sauver, and P. Angulo. 2012. The Framingham risk score and heart disease in nonalcoholic fatty liver disease. Liver Int 32: 945-950;

Utzschneider et al., 2006, J. Clin. Endocrinol. Metab. 91:4753-4761;

Uysal, K. T., S. M. Wiesbrock, M. W. Marino, and G. S. Hotamisligil. 1997. Protection from obesity-induced insulin resistance in mice lacking TNF-alpha function. Nature 389: 610-614;

Wei, Z., X. Lei, M. M. Seldin, and G. W. Wong. 2012. Endopeptidase cleavage generates a functionally distinct isoform of C1q/tumor necrosis factor-related protein-12 (CTRP12) with an altered oligomeric state and signaling specificity. J Biol Chem 287: 35804-35814;

Wei, Z., J. M. Peterson, X. Lei, L. Cebotaru, M. J. Wolfgang, G. C. Baldeviano, and G. W. Wong. 2012. C1q/TNF-related protein-12 (CTRP12), a novel adipokine that improves insulin sensitivity and glycemic control in mouse models of obesity and diabetes. J Biol Chem 287: 10301-10315;

Wei, Z., J. M. Peterson, and G. W. Wong. 2011. Metabolic regulation by C1q/TNF-related protein-13 (CTRP13): activation OF AMP-activated protein kinase and suppression of fatty acid-induced JNK signaling. J Biol Chem 286: 15652-15665;

Wolfing, B., C. Buechler, J. Weigert, M. Neumeier, C. Aslanidis, J. Schoelmerich, and A. Schaffler. 2008. Effects of the new C1q/TNF-related protein (CTRP-3) "cartonectin" on the adipocytic secretion of adipokines. Obesity (Silver Spring) 16: 1481-1486;

Wong, G. W., P. S. Foster, S. Yasuda, J. C. Qi, S. Mahalingam, E. A. Mellor, G. Katsoulotos, L. Li, J. A. Boyce, S. A. Krilis, and R. L. Stevens. 2002. Biochemical and functional characterization of human transmembrane tryptase (TMT)/tryptase gamma TMT is an exocytosed mast cell protease that induces airway hyperresponsiveness in vivo via an interleukin-13/interleukin-4 receptor alpha/signal transducer and activator of transcription (STAT) 6-dependent pathway. J Biol Chem 277: 41906-41915;

Wong, G. W., S. A. Krawczyk, C. Kitidis-Mitrokostas, G. Ge, E. Spooner, C. Hug, R. Gimeno, and H. F. Lodish. 2009. Identification and characterization of CTRP9, a novel secreted glycoprotein, from adipose tissue that reduces serum glucose in mice and forms heterotrimers with adiponectin. FASEB J 23: 241-258;

Wong, G. W., S. A. Krawczyk, C. Kitidis-Mitrokostas, T. Revett, R. Gimeno, and H. F. Lodish. 2008. Molecular, biochemical and functional characterizations of C1q/TNF family members: adipose-tissue-selective expression patterns, regulation by PPAR-gamma agonist, cysteine-mediated oligomerizations, combinatorial associations and metabolic functions. Biochem J 416: 161-177;

Wong, G. W., J. Wang, C. Hug, T. S. Tsao, and H. F. Lodish. 2004. A family of Acrp30/adiponectin structural and functional paralogs. Proc Natl Acad Sci USA 101: 10302-10307;

Wu, J. W., S. P. Wang, F. Alvarez, S. Casavant, N. Gauthier, L. Abed, K. G. Soni, G. Yang, and G. A. Mitchell. 2011. Deficiency of liver adipose triglyceride lipase in mice causes progressive hepatic steatosis. Hepatology 54: 122-132;

Xu, A., Y. Wang, H. Keshaw, L. Y. Xu, K. S. Lam, and G. J. Cooper. 2003. The fat-derived hormone adiponectin alleviates alcoholic and nonalcoholic fatty liver diseases in mice. J Clin Invest 112: 91-100;

Yamauchi, T., J. Kamon, H. Waki, Y. Terauchi, N. Kubota, K. Hara, Y. Mori, T. Ide, K. Murakami, N. Tsuboyama-Kasaoka, O. Ezaki, Y. Akanuma, O. Gavrilova, C. Vinson, M. L. Reitman, H. Kagechika, K. Shudo, M. Yoda, Y. Nakano, K. Tobe, R. Nagai, S. Kimura, M. Tomita, P. Froguel, and T. Kadowaki. 2001. The fat-derived hormone adiponectin reverses insulin resistance associated with both lipoatrophy and obesity. Nat Med 7: 941-946;

Yen, C. L., S. J. Stone, S. Koliwad, C. Harris, and R. V. Farese, Jr. 2008. Thematic review series: glycerolipids. DGAT enzymes and triacylglycerol biosynthesis. J Lipid Res 49: 2283-2301; and Yi, W., Y. Sun, Y. Yuan, W. B. Lau, Q. Zheng, X. Wang, Y. Wang, X. Shang, E. Gao, W. J. Koch, and X. L. Ma. 2012. C1q/tumor necrosis factor-related protein-3, a newly identified adipokine, is a novel antiapoptotic, proangiogenic, and cardioprotective molecule in the ischemic mouse heart. Circulation 125: 3159-3169.

Although the foregoing subject matter has been described in some detail by way of illustration and example for purposes of clarity of understanding, it will be understood by those skilled in the art that certain changes and modifications can be practiced within the scope of the appended claims.

---

That which is claimed:

1. A method for treating or preventing the progression of fatty liver disease in a subject in need thereof, the method comprising administering to the subject a therapeutically effective amount of a C1q/TNF-related protein 3 (CTRP3) polypeptide or a functional variant thereof, wherein the CTRP3 polypeptide or functional variant thereof comprises at least 90% identity to the amino acid sequence of SEQ ID NO: 1 or SEQ ID NO: 3.

2. The method of claim 1, wherein the CTRP3 polypeptide or functional variant thereof is a functional fragment at least 90% identical to the amino acid sequence of SEQ ID NO:1 or SEQ ID NO:3.

3. The method of claim 1, wherein the CTRP3 polypeptide or functional variant thereof is fused to an epitope tag.

4. The method of claim 3, wherein the epitope tag is placed at a carboxyl-terminus of the CTRP3 polypeptide.

5. The method of claim 4, wherein the epitope tag is a Flag-polypeptide tag.

6. The method of claim 1, wherein the fatty liver disease is selected from the group consisting of non-alcoholic fatty liver disease (NAFLD), alcoholic fatty liver disease (AFLD), non-alcoholic steatohepatitis (NASH), alcoholic steatohepatitis (ASH), NASH-associated liver fibrosis, ASH-associated liver fibrosis, non-alcoholic cirrhosis, and alcoholic cirrhosis.

7. The method of claim 6, wherein the fatty liver disease is non-alcoholic fatty liver disease (NAFLD).

8. The method of claim 1, wherein the subject is a human.

* * * * *